(12) United States Patent
Zaghloul et al.

(10) Patent No.: US 8,143,681 B2
(45) Date of Patent: Mar. 27, 2012

(54) SAW DEVICES, PROCESSES FOR MAKING THEM, AND METHODS OF USE

(75) Inventors: Mona Zaghloul, Bethesda, MD (US); Onur Tigli, Vancouver, WA (US); Anis Nurashikin Nordin, Selangor (MY)

(73) Assignee: The George Washington University, Washington, DC (US)

( * ) Notice: Subject to any disclaimer, the term of this patent is extended or adjusted under 35 U.S.C. 154(b) by 980 days.

(21) Appl. No.: 11/738,460

(22) Filed: Apr. 20, 2007

(65) Prior Publication Data
US 2008/0230859 A1    Sep. 25, 2008

Related U.S. Application Data

(60) Provisional application No. 60/793,328, filed on Apr. 20, 2006.

(51) Int. Cl.
*H01L 29/84*    (2006.01)
(52) U.S. Cl. .............. 257/416; 257/E45.006; 310/313 B
(58) Field of Classification Search .................. 257/416, 257/E45.006; 310/313 B–313 D
See application file for complete search history.

(56) References Cited

U.S. PATENT DOCUMENTS

| | | |
|---|---|---|
| 4,065,735 A | 12/1977 | Palfreeman et al. |
| 4,065,736 A * | 12/1977 | London ........................ 333/196 |
| 4,124,828 A * | 11/1978 | Bert ............................. 333/153 |
| 4,194,171 A * | 3/1980 | Jelks ............................ 333/149 |
| 4,354,166 A | 10/1982 | Grudkowski |
| 4,387,355 A | 6/1983 | Uno et al. |
| 4,453,242 A | 6/1984 | Toda |
| 4,647,881 A | 3/1987 | Mitsutsuka |
| 4,665,374 A * | 5/1987 | Fathimulla ................... 333/196 |
| 5,166,646 A | 11/1992 | Avanic et al. |
| 5,196,720 A * | 3/1993 | Sugai et al. .................. 257/254 |

(Continued)

FOREIGN PATENT DOCUMENTS
WO    WO 2004012331 A1 *    2/2004

OTHER PUBLICATIONS

Buff et al.; "Universal pressure and temperature SAW sensor for wireless applications," Ultrasonics Symposium, 1997. Proceedings., 1997 IEEE , vol. 1, No. pp. 359-362 vol. 1, Oct. 5-8, 1997.

(Continued)

*Primary Examiner* — Allan R Wilson
(74) *Attorney, Agent, or Firm* — Panitch Schwarze Belisario & Nadel LLP

(57) ABSTRACT

The design, fabrication, post-processing and characterization of a novel SAW (Surface Acoustic Wave) based bio/chemical sensor in CMOS technology is introduced. The sensors are designed in AMI 1.5 μm 2 metal, 2 poly process. A unique maskless post processing sequence is designed and completed. The three post-processing steps are fully compatible with any CMOS technology. This allows any signal control/processing circuitry to be easily integrated on the same chip. ZnO is used as the piezoelectric material for the SAW generation. A thorough characterization and patterning optimization of the sputtered ZnO was carried out. The major novelties that are introduced in the SAW delay line features are: The embedded heater elements for temperature control, compensation and acoustic absorbers that are designed to eliminate edge reflections and minimize triple transit interference. Both of these attributes are designed by using the CMOS layers without disturbing the SAW performance.

13 Claims, 25 Drawing Sheets

U.S. PATENT DOCUMENTS

| | | | |
|---|---|---|---|
| 5,214,338 | A | 5/1993 | Tanski |
| 5,235,233 | A | 8/1993 | Yamamoto |
| 5,265,267 | A | 11/1993 | Martin et al. |
| 5,477,098 | A | 12/1995 | Eguchi et al. |
| 5,559,483 | A | 9/1996 | Kajihara et al. |
| 5,571,401 | A | 11/1996 | Lewis et al. |
| 6,285,866 | B1 | 9/2001 | Lee et al. |
| 6,336,368 | B1 | 1/2002 | Chung et al. |
| 6,404,101 | B1 | 6/2002 | Taniguchi et al. |
| 6,407,486 | B1 | 6/2002 | Kimura et al. |
| 6,448,064 | B1 | 9/2002 | Vo-Dinh et al. |
| 6,495,892 | B2 | 12/2002 | Goodman et al. |
| 6,518,084 | B1 | 2/2003 | Seitz et al. |
| 6,555,946 | B1 | 4/2003 | Finder et al. |
| 6,580,198 | B2 | 6/2003 | Nakano et al. |
| 6,621,134 | B1 | 9/2003 | Zurn |
| 6,627,154 | B1 | 9/2003 | Goodman et al. |
| 6,657,269 | B2 | 12/2003 | Migliorato et al. |
| 6,686,675 | B2 | 2/2004 | Koshido |
| 6,743,581 | B1 | 6/2004 | Vo-Dinh |
| 6,842,091 | B2 | 1/2005 | Yip |
| 6,861,754 | B2 | 3/2005 | Lin et al. |
| 6,872,902 | B2 | 3/2005 | Cohn et al. |
| 6,877,209 | B1 | 4/2005 | Miller et al. |
| 6,933,808 | B2 | 8/2005 | Ma et al. |
| 6,937,052 | B2 | 8/2005 | Tam |
| 6,937,114 | B2 | 8/2005 | Furukawa et al. |
| 6,951,047 | B2 | 10/2005 | Tomioka et al. |
| 7,170,213 | B2 | 1/2007 | Yamanaka et al. |
| 7,295,089 | B2 | 11/2007 | Shibahara et al. |
| 7,301,423 | B2 | 11/2007 | Furuhata et al. |
| 7,369,014 | B1 | 5/2008 | Fehsenfeld et al. |
| 7,400,219 | B2 * | 7/2008 | Furuhata et al. .............. 333/193 |
| 7,473,551 | B2 | 1/2009 | Warthoe |
| 7,498,898 | B2 | 3/2009 | Nakanishi et al. |
| 7,647,814 | B2 | 1/2010 | Nakaso et al. |
| 2002/0041218 | A1 | 4/2002 | Tonegawa et al. |
| 2003/0231082 | A1 | 12/2003 | Takata et al. |
| 2004/0021403 | A1 | 2/2004 | Ayazi et al. |
| 2004/0070312 | A1 | 4/2004 | Penunuri et al. |
| 2004/0110299 | A1 | 6/2004 | Sivavec |
| 2004/0178698 | A1 | 9/2004 | Shimoe et al. |
| 2004/0189148 | A1 | 9/2004 | Yamanaka et al. |
| 2004/0232802 | A1 * | 11/2004 | Koshido ........................ 310/348 |
| 2004/0245891 | A1 * | 12/2004 | Kawachi et al. .......... 310/313 R |
| 2005/0017896 | A1 | 1/2005 | Klofer et al. |
| 2005/0029960 | A1 | 2/2005 | Roh et al. |
| 2005/0043894 | A1 | 2/2005 | Fernandez |
| 2005/0131998 | A1 | 6/2005 | Takashima |
| 2005/0242891 | A1 | 11/2005 | Ash |
| 2005/0281210 | A1 | 12/2005 | Makino |
| 2006/0032312 | A1 | 2/2006 | Auner et al. |
| 2006/0131678 | A1 | 6/2006 | Yajima et al. |
| 2006/0197408 | A1 | 9/2006 | Chen |
| 2006/0230833 | A1 * | 10/2006 | Liu et al. ......................... 73/649 |
| 2007/0159027 | A1 | 7/2007 | Tsai et al. |
| 2010/0029226 | A1 | 2/2010 | Visser |

OTHER PUBLICATIONS

Smole et al.; "Magnetically tunable SAW-resonator," Frequency Control Symposium and PDA Exhibition Jointly with the 17th European Frequency and Time Forum, 2003. Proceedings of the 2003 IEEE International , vol., No. pp. 903-906, May 4-8, 2003.

Pohl et al.; "Wireless sensing using oscillator circuits locked to remote high-Q SAW resonators," Ultrasonics, Ferroelectrics and Frequency Control, IEEE Transactions on , vol. 45, No. 5pp. 1161-1168, Sep. 1998.

Nomura et al.; "Chemical sensor based on surface acoustic wave resonator using Langmuir-Blodgett film", Ultrasonics, Ferroelectrics and Frequency Control, IEEE Transactions on , vol. 45, No. 5pp. 1261-1265, Sep. 1998.

Datta; "Resonators", Prentice Hall, 1986, Ch. 10, pp. 225-239.

Ruby et al.; "Thin film bulk wave acoustic resonators (FBAR) for wireless applications," Ultrasonics Symposium, 2001 IEEE , vol. 1, No. pp. 813-821 vol. 1, 2001.

Visser, "Surface acoustic wave filter in ZnO-SiO2-Si layered structures: Design, technology and monolithic integration with electronic circuitry," Ph.D. dissertation, Delft University of Technology. Delft, the Netherlands, Dec. 1989.

Vellekoop et al.; "Acoustic-wave based monolithic unicrosensors", Invited, Proc. IEEE Ultrasonics Symposium, Cannes, France, (1994), pp. 565-574.

Baca et al.; "Development of a GaAs monolithic surface acoustic wave integrated circuit", IEEE J. Solid-State Circuits, vol. 34. No. 9, 1999.

Nordin et al.; "Design and Implementation of a 1 GHz Resonator Utilizing Surface Acoustic Wave," presented at the Int. Sym. Circuits and Systems, Kos, Greece, 2006.

Morgan "Analysis of Interdigital Transducers," Surface-Wave Devices for Signal Processing, New York: Elesevier Science, 1985, Ch. 4, pp. 57-105.

vanZeijl, "Fundamental aspects and design of an FM upconversion receiver front-end with on-chip SAW filters," Ph. D. dissertation, Delft University of Technology. Delft, Netherlands, Feb. 1990.

Datta et al.; "An analytical theory for the scattering of surface acoustic waves by a single electrode in a periodic array on a piezoelectric substrate", J.Appl.Phys, vol. 51, pp. 4817-4823, Sep. 1980.

Tigli et al.; "Design and Fabrication of a Novel SAW Bio/Chemical Sensor in CMOS", in 2005 Proc. IEEE Sensors Conf., pp. 137-140.

Vellekoop; "A Smart Lamb-Wave Sensor System", Ph.D. dissertation, Delft University of Technology. Delft, the Netherlands, Dec. 1989.

Zhu et al.; "Wet-Chemical Etching of (112-?0) ZnO Films", Journal of Electronic Materials; Jun 2004, vol. 33, No. 6, pp. 556-559.

Standard definitions and methods of measurement for piezoelectric vibrators, ANSI/IEEE Standard 177, New York, NY, May 1966.

IEEE Standard on Piezoelectricity, ANSI/IEEE Standard 176, New York, NY, 1987.

Iwai; 2000, "CMOS technology for RF application", Proc. 22nd International Conference on Microelectronics (MIEL ZOOO), vol. 1, Ni$, Serbia, May 14-17, 2000, 1, pp. 27-34 vol. 21.

Hassan et al.; 2004, "Impact of technology scaling on RF CMOS", IEEE Soc Conference pp. 97-101.

Burghartz; 2001, "Tailoring logic CMOS for RF applications", VLSI Technology Systems and Applications, pp. 150-153.

Bingxue; 2001, "Challenges in RF analog integrated circuits", ASIC, IEEE Proceedings. 4th International Conference on, pp. 800-805.

Iwai; 2004, "RF CMOS technology", Radio Science Conference, IEEE Proceedings Asia-Pacific, pp. 296-298.

Huang et al.; "The impact of scaling down to deep submicron on CMOS RF circuits," Solid-State Circuits, IEEE Journal of, Jul. 1998, 33(7), pp. 1023-1036.

Steyaert et al.; "Low-voltage low-power CMOS-RF transceiver design," Microwave Theory and Techniques, IEEE Transactions on, 2002, 50, (1), pp. 281-287.

Lin et al.; 1998, "Micropower CMOS RF components for distributed wireless sensors", Radio Frequency Integrated Circuits (RFIC) Symposium, IEEE, pp. 157-160.

Campbell, "Surface Acoustic Wave Devices for Mobile and Wireless Communications," Academic Press, 1998, pp. 114-122.

Tan et al.,"Minmization of Diffraction Effects in Saw Devices Using a Wide Aperture," Ultrasonics Symposium, 1986, pp. 13-17.

Nakagawa, "A New Saw Convolver Using Multi-Channel Waveguide," Ultrasonics Symposium, 1991, pp. 255-258.

Green et al., "Focused Surface Wave Transducers on Aniosotropic Substrates: A Theory for the Waveguided Storage Correlator" Ultrasonics Symposium, 1980, pp. 69-73.

Wilcox et al., "Time-Fourier transform by a focusing array of phased surface acoustic wave transducers," J. Appl., Phys. vol. 58, No. 3, Aug. 1985, pp. 1148-1159.

Brooks et al., Saw RF Spectrum Analyzer/Channelizer Using a Focusing, Phased Array Transducer, Ultrasonics Symposium, 1985, pp. 91-95.

Wu et al., "Analysis and Design of Focused Interdigital Transducers," IEEE Transactions on Ultrasonics, Ferroelectrics, and Frequency Control, vol. 52, No. 8, Aug. 2005, pp. 1384-1392.

Qiao et al., "Focusing of Surface Acoustic Wave on a Piezoelectric Crystal," Chin. Phys. Lett., vol. 23, No. 7, 2006, pp. 1834-1837.

Fang et al., "SAW Focusing by Circular-Arc Interdigital Transducers on YZ-LiNbO3," IEEE Transactions on Ultrasonics, Ferroelectrics, and Frequency Control, vol. 36, No. 2, Mar. 1989, pp. 178-184.

Kharusi et al., "On Diffraction and Focusing in Anistropic Crystals," Proceedings of the IEEE, vol. 60, No. 8, Aug. 1972, pp. 945-956.

Oezguer et al., "A comprehensive review of ZnO materials and devices," Journal of Applied Physics, vol. 98, Aug. 2005, pp. 041301-1-041301-103.

Tigli et al., "A Novel Saw Device in CMOS: Design, Modeling, and Fabrication," IEEE Sensors Journal, vol. 7, No. 2, Feb. 2007, pp. 219-227.

Tigli et al., "Design and Fabrication of a novel SAW Bio/Chemical Sensor in CMOS," IEEE Sensors Journal, Oct. 2005, pp. 137-140.

Coventor, 3D MEMS Design Automation & Virtual Fabrication—Coventor at http:www.coventor.com.

Tigli et al., "Design, Modeling, and Characterization of a Novel Circular Surface Acoustic Wave Device," IEEE Sensors Journal, vol. 8, No. 11, Nov. 2008, pp. 1807-1815.

Tigli et al., "A Novel Circular SAW (Surface Acoustic Wave) Device in CMOS," IEEE Sensors Journal, 2007, pp. 474-477.

Vellekoop et al.; "Acoustic-wave based monolithic microsensors", Invited, Proc. IEEE Ultrasonics Symposium, Cannes, France, (1994), pp. 565-574.

Morgan, "Surface-Wave Devices for Signal Processing," Studies in Electrical and Electronic Engineering 19, 1985, pp. 129-155.

Farnell, "Elastice Surface Waves," Surface Wave Filters; Design, Construction, and Use, 1977, pp. 1-53.

U.S. Appl. No. 12/405,503, filed Mar. 17, 2009, George Washington University.

U.S. Appl. No. 12/166,646, filed Jul. 2, 2008, George Washington University.

U.S. Appl. No. 12/166,601, filed Jul. 2, 2008, George Washington University.

Office Action issued May 26, 2011 in U.S. Appl. No. 12/405,503.

Yamanouchi, "GHz-Range SAW Device Using Nano-Meter Electrode Fabrication Technology", IEEE Ultrasonics Symposium Proceedings, vol. 1, pp. 421-428 (1994).

Nordin et al, "CMOS Surface Acoustice Wave Oscillators", IEEE 48th Midwest Symposium on Circuits and Systems, pp. 607-610 (2005).

Office Action issued Aug. 16, 2011 in U.S. Appl. No. 12/166,601.

Office Action Issued Jan. 14, 2011 in U.S. Appl. No. 12/166,646.

* cited by examiner

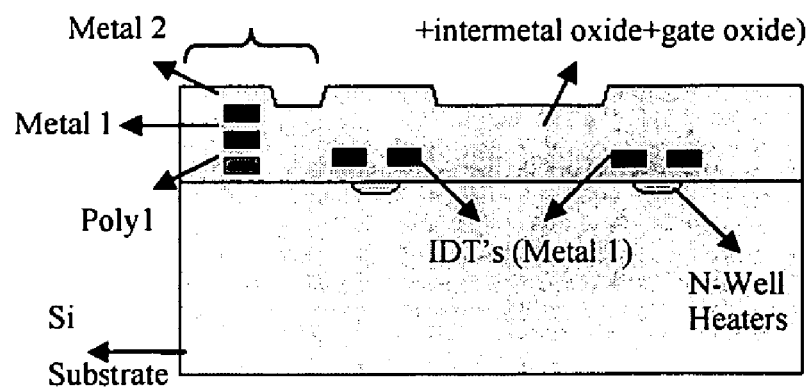
Figure 3.
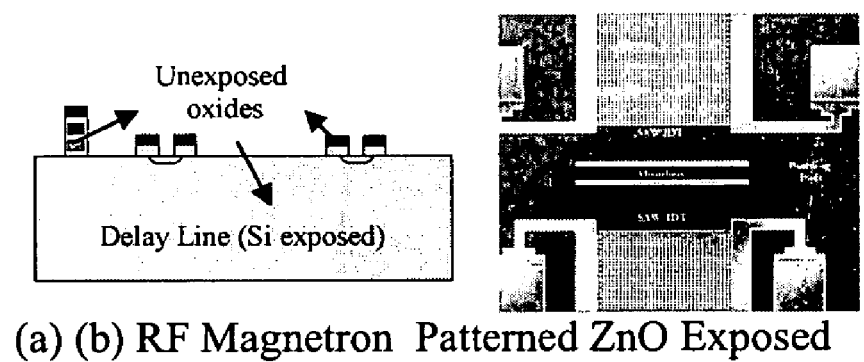
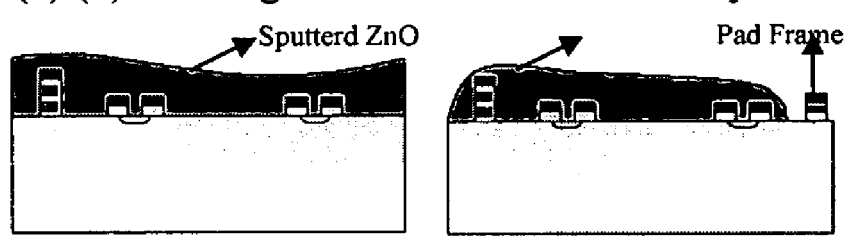
Figure 4.

(a)

(b)

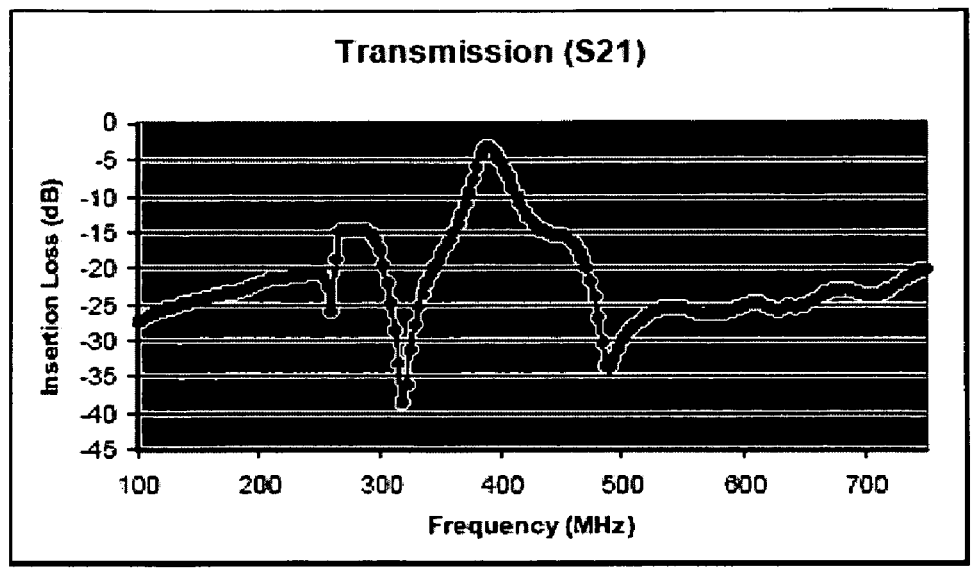
(a)
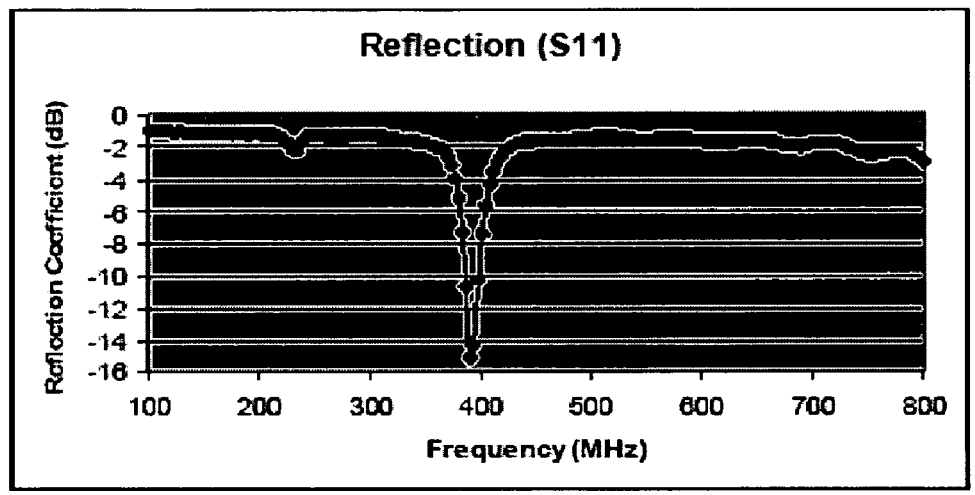
(b)
Figure 6. (a) The Insertion Loss vs. Frequency. Note that the center frequency fc = 392.5 MHz and the minimum loss at fc is -4.93 dB (b) The reflection coefficient vs. Frequency.

(a) Cross-section of CMOS SAW resonator designs 1 and 2 utilizing two CMOS metal layers.
(b) Cross-section of CMOS SAW resonator design 3 utilizing three CMOS metal layers.

Figure 11

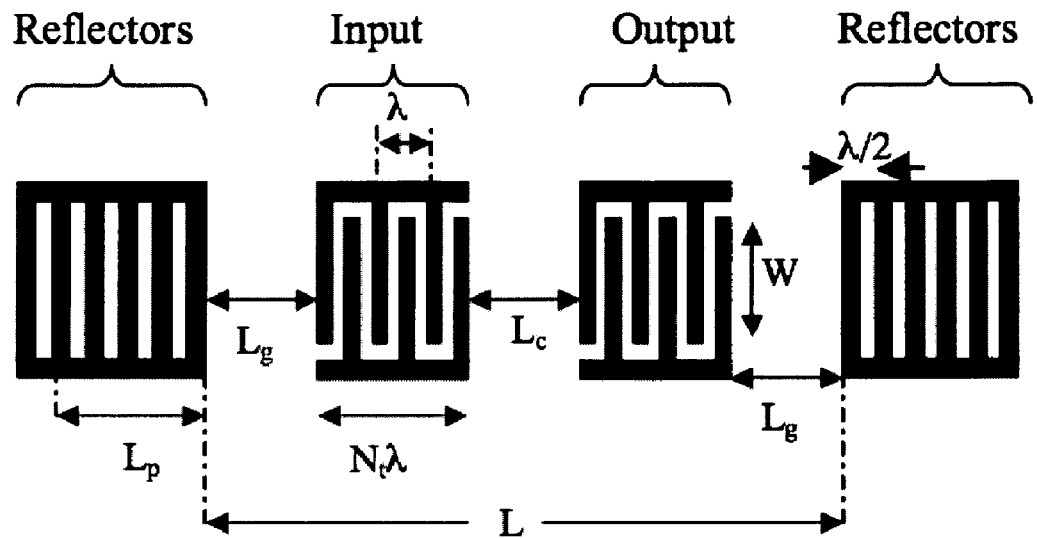

Key design parameters and equations for a two-port resonator.
fr : Resonant frequency
$\lambda$ : periodic distance of interdigital fingers
v : Acoustic wave velocity = fr . $\lambda$
$\zeta$ : metal width = $\lambda/4$
$\eta$ : Metallization ratio = 0.5
W : Width of aperture
N : Number of reflectors
Nt : Number of transducer pairs
Lg : Distance between reflector and transducer
Lc : Distance between input and output transducers
L : Distance between reflectors
Lp : Effective penetration length Resonator's interdigital transducers and reflectors after reactive-ion etch. Inset: Cross-section of etched interdigital fingers.

X-Ray Diffraction 2θι-scan of CMOS resonator chip. Height of ZnO (002) is 2.9 cps.

SEM and microscope image of CMOS SAW resonator 2. (a) Etched edge of ZnO. (b) Resonator 2 after ZnO etching. (c) Acid wet-etch process where resonator is masked using photoresist.

(a)

(b)

$C_t$ : Static capacitance between $IDT_{in}$ and $IDT_{gnd}$
$C_{ox}$: Oxide capacitance between $IDT_{in}$ and ground shield
$C_f$ : Capacitance between $IDT_{in}$ and $IDT_{out}$.

(a) Cross section of CMOS fabrication layers and equivalent circuit model of the two-port acoustic wave resonator. (b) Top view and schematic of the acoustic wave resonator.

Harmonic analysis of CMOS SAW resonator design 1 with λ=3.6μm using CoventorWare(R).
For this device, the resonant frequency was at 1.13 GHz.

Microscope image of whole chip consisting of three resonators and Thru calibration structure.

(a) Experimental setup: Device under test measured using coplanar G-S-G probes connected to the HP8712 (300 kHz to 1.13 GHz). (b) Snapshot of measurement arrangement.

Fig. 12. $S_{11}$ measurement results of three resonators. (a) Resonator 1 (b) Resonator 2 (c) Resonator 3

$S_{21}$ Magnitude Transmission characteristics of Resonator 1.

$S_{21}$ Magnitude Transmission characteristics of Resonator 2.

$S_{21}$ Magnitude Transmission characteristics of Resonator 3.

SAW DEVICES, PROCESSES FOR MAKING THEM, AND METHODS OF USE

PRIORITY

This application claims priority under 119(e) to U.S. 60/793,328 filed 20 Apr. 2006.

GOVERNMENT INTEREST

This was supported in part by NSF under Grant 0225431.

BACKGROUND

1. Field of the Invention

The present invention relates to the field of surface acoustic wave (SAW) devices, and specifically to improvements to in their manufacturing which then provides additional applications for use.

2. Description of the Prior Art

Acoustic wave sensors use a detection arrangement that is based on perturbations to mechanical or acoustic waves. As an acoustic wave propagates through or on the surface of the acoustive wave sensor material, any changes to the physical or chemical characteristics of the wave path may affect the velocity and/or amplitude of the acoustic wave. These changes may be correlated to the corresponding physical, chemical, or biological quantities being measured to provide sensing.

There may be various biological and chemical sensors, using fiber optics, chemical interactions, and various fluorescence approaches. Such sensors may, however, have various weaknesses, such as, for example, low sensitivity, selectivity, or an inability to be hybridized or integrated into sensing chip technology. Acoustic wave (AW) sensors, however, may be better suited for use in biological and chemical detection. As discussed in D. S. Ballantine, R. M. White, S. J. Martin, A. J. Ricco, E. T. Zellers, G. C. Frye, H. Wohltjen, "Acoustic Wave Sensor—Theory, Design, and Physico-Chemical Applications", Academic Press, (1997), acoustic wave sensors may use piezoelectric crystals, which may allow transduction between electrical and acoustic energies. The AW sensor may use piezoelectric material to convert a high frequency signal into an acoustic wave, and the higher frequency may enable the sensor to be more sensitive to surface perturbations.

Piezoelectric materials used for acoustic wave sensors may include quartz ($SiO_2$), lithium niobate ($LiNbO_3$), zinc oxide (ZnO), and others. Each of these materials may possess specific advantages and disadvantages, which may relate to, for example, cost, temperature dependence, attenuation, and propagation velocity. Such materials may, however, have varying transverse acoustic wave velocities, low electromechanical coupling coefficients, non-linear temperature coefficients, and may react chemically with the environment. (See the background information in C. Caliendo, G. Saggio, P. Veradi, E. Verona, "Piezoelectric AlN Film for SAW Device Applications", Proc. IEEE Ultrasonic Symp., 249-252, (1992) and K. Kaya, Y. Kanno, I. Takahashi, Y. Shibata, T. Hirai, "Synthesis of AlN Thin Films on Sapphire Substrates by Chemical Vapor Deposition of $AlCl_3$—$NH_3$ Systems and Surface Acoustic Wave Properties", Jpn. J. Appl. Phys. Vol. 35, 2782-2787, (1996) and G. Carlotti et al., "The Elastic Constants of Sputtered AlN Films", Proc. IEEE Ultrasonic Symp., 353, (1992)).

Previously, creation of SAW devices has been complicated and, in the case of CMOS fabrication, it has been unworkable as the chip would be destroyed by the temperatures required to integrate the SAW device.

SUMMARY

Provided is an integrated circuit chip having a SAW device as an on-chip component. In preferred embodiments, the chip can be a microprocessor, a programmable integrated circuit, a microelectromechanical system (MEMS), and a nanoelectromechanical system (NEMS).

In one embodiment, an integrated circuit chip is provided which has an embedded heater structure.

In another preferred embodiment, a SAW device having an absorber structure which comprise CMOS layers of metal1, metal2, and polysilicon is provided.

Also provided in a preferred embodiment is an LC circuit, or TANK circuit, which comprises a SAW device and an amplifier on the same chip. In another embodiment, a local oscillator is provided, which comprises an LC circuit connected to a Pierce oscillator.

SAW resonators fabricated using CMOS technology are also contemplated as within the scope of the invention.

Preferred processes for fabricating a SAW device using standard CMOS technology are also contemplated, comprising the steps of: i) depositing piezoelectric material on top of SAW IDT's, and ii) performing a wet-etching of the piezoelectric material to expose the pads for bonding, wherein the SAW IDT's are patterned on the dielectric layer during CMOS fabrication and a reactive ion etch releases the IDT's from the dielectric layer before the piezoelectric material is deposited.

In preferred processes, the piezoelectric material is ZnO, the wet-etching uses a very dilute acid solution, and wherein the very dilute acid solution is a two acid mixture, wherein each acid of the two acid mixture is selected from the group consisting of acetic acid, hydrochloric acid, and phosphoric acid.

Additional preferred processes include wherein the CMOS process sequence includes fabricating an absorber structure on the SAW device designed from stacking CMOS layers of metal1, metal2 and polysilicon to achieve a surface higher than the IDT level for attenuating or reflecting the acoustic waves.

SAW devices made by the processes herein are also within the scope of the invention.

A heat control structure built within the substrate silicon during the CMOS process is also part of the inventive subject matter and can be adopted in any of the CMOS chip devices herein. In preferred embodiments, the heat control structure is an n-well layer that has a TCR of 0.5-0.75%/K, which is the highest among various CMOS process layers and wherein the n-well provides an embedded heater structure that can directly control the temperature of the substrate and the mass sensitive area without causing any disturbance on the SAW delay line path or the IDT finger design.

Preferred uses of the devices herein include SAW based integrated circuit detection systems which comprise: a sensor having at least one sensing element for selectively combining with target molecules, said sensor generating a signal when combined with said target molecules responsive to incident electromagnetic radiation applied to said sensor/target combination; and an integrated circuit microchip to which the sensor is affixed, the integrated circuit microchip including: a plurality of detection channels operatively associated with said sensing elements, each of said detection channels including a detector for detecting electromagnetic signals, said detectors selected from the group consisting of photodiodes and phototransistors. In preferred uses the sensor comprises a chemical receptor, a bioreceptor, a polymer, a biopolymer, a molecular imprint polymer, a biomimetic, an antibody, an enzyme, a cell receptor, a molecular print assay, or a nucleic acid.

For detection of the target, phase shift detection or alternatively frequency shift detection can be used within the SAW device.

The systems herein can also preferably be implemented in a hand held unit. Thus, as oscillator or filter etc. or alternatively as a bio/chemical sensing device.

Provided is a process for fabricating a SAW device using CMOS technology, comprising: designing and fabricating a SAW IDT through a regular CMOS process sequence to obtain a SAW device; performing a reactive ion etch on the SAW device; performing a maskless sputtering from the front to the SAW device using ZnO, wherein the ZnO covers the entire surface including the IDT fingers and the exposed Si; etching the SAW device using a simple shadow mask, wherein the mask is constructed using a Si, and wherein the photoresist build up covering the pad frame is completely removed by i) exposing the device after spincoating with a photoresist, applying developer, and ii) performing a second exposure and development to remove the excessive photoresist using the same exposure time and development time, and wherein the etching process is slowed using a very dilute acid solution.

The process can also include wherein the CMOS process sequence includes fabricating an absorber structure designed from stacking CMOS layers of metal1, metal2 and polysilicon to achieve a surface higher than the IDT level for attenuating or reflecting the acoustic waves.

The process also contemplates wherein etching the SAW device using a simple shadow mask comprises wherein the mask is constructed using a square Si piece of size 2×2 mm, and wherein the photoresist build up covering the pad frame is completely removed by exposing the device for about 20 seconds after spinning a Shipley 1818 2:1 thinner for 40 sec at 5000 rpm, wherein a 2 min development in 5:1 Developer is applied, and performing a second exposure and development to remove the excessive photoresist using the same exposure time and development time, and wherein the etching process is slowed using a very dilute solution of a two acid mixture, wherein each acid of the two acid mixture is selected from the group consisting of acetic acid, hydrochloric acid, and phosphoric acid.

Another preferred embodiment of the invention includes a SAW device made by the processes described herein, especially those wherein signal control and processing circuitry are integrated on the same chip, and those wherein the n-well layer has a TCR of 0.5-0.75%/K, which is the highest among various CMOS process layers and wherein the n-well provides an embedded heater structure that can directly control the temperature of the substrate and the mass sensitive area without causing any disturbance on the SAW delay line path or the IDT finger design.

A further preferred embodiment includes a SAW based integrated circuit based detection system comprising: a sensor having at least one sensing element for selectively combining with target molecules, said sensor generating a signal when combined with said target molecules responsive to incident electromagnetic radiation applied to said biosensor/target combination; and an integrated circuit microchip to which the sensor is affixed, the integrated circuit microchip including: a plurality of detection channels operatively associated with said sensing elements, each of said detection channels including a detector for detecting electromagnetic signals, said detectors selected from the group consisting of photodiodes and phototransistors.

Preferably, the integrated circuit includes wherein the sensor comprises a chemical receptor, a bioreceptor, a polymer, a biopolymer, a molecular imprint polymer, a biomimetic, an antibody, an enzyme, a cell receptor, a molecular print assay, or a nucleic acid.

It is believed that advantages of the exemplary embodiments and/or exemplary methods of the present invention may include optimized biosensor devices, improved biosensor arrangement performance, determination of effective sensing media immobilization approaches, and SAW based biosensors that may be used to provide continuous, in-situ, and rapid detection and quantification of analytes in samples.

BRIEF DESCRIPTION OF THE FIGURES

FIG. 3. Side view of the die, fabricated in AMI 1.5 μm technology.

FIG. 4. Side-view of the die after the (a) Reactive Ion Etching of the dielectrics (b) SEM of IDTs after RIE (c) ZnO deposition on the entire die (d) ZnO etching.

FIG. 6 (a) The insertion Loss vs. Frequency. Note that the center frequency fc=392.5 MHz and the minimum loss at fc is −4.93 dB (b) The Reflection Coefficient vs. Frequency.

FIG. 11 is a graphic and shows key design parameters and equations for a two-port resonator.

DETAILED DESCRIPTION OF THE PREFERRED EMBODIMENTS

CMOS is short for complementary metal oxide semiconductor. Pronounced see-moss, CMOS is a widely used type of semiconductor. CMOS semiconductors use both NMOS (negative polarity) and PMOS (positive polarity) circuits. Since only one of the circuit types is on at any given time, CMOS chips require less power than chips using just one type of transistor. This makes them particularly attractive for use in battery-powered devices, such as portable computers. Personal computers also contain a small amount of battery-powered CMOS memory to hold the date, time, and system setup parameters.

SAW (surface acoustic wave) devices are widely used as electronic filters, delay lines, resonators in today's communication systems. Although telecommunication industry is the largest user of these devices, SAW based sensors have many attractive features to be explored for emerging technologies in automotive (torque, pressure), medical (biosensor) and commercial (vapor, gas, humidity) applications.

Figure 1:
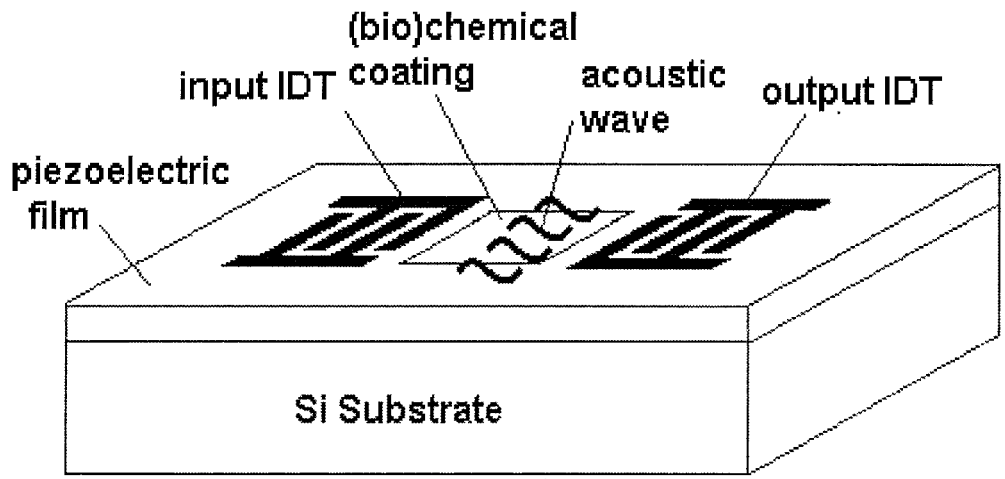
FIG. 1. Basic principle of a SAW based bio/chemical sensor employing the mass loading scheme. This architecture (i.e. IDTs on top of the piezoelectric material) is the most common architecture.

Surface acoustic waves (both Rayleigh and pseudo-SAW) are generated at the free surface of a piezoelectric material. An application of a varying voltage to the metal IDT (interdigital transducer) generates the acoustic wave on the input side. In the basic configuration there is an input IDT and an output IDT. The acoustic wave generated by the input IDT travels through the region called the delay line and reaches the output IDT where the mechanical displacements due to the acoustic waves create a voltage difference between the output IDT fingers. One of the most widely used and interesting sensing mechanism that acoustic wave sensors employ is mass loading. Prominent applications are in film thickness monitoring, gas, liquid phase chemical sensing and biosensing. The delay lines of SAW devices are coated with some bio/chemical coating which selectively reacts with the entity under analysis. This interaction produces a shift in the resonant frequency of the SAW device. By measuring this shift in frequency domain, a detailed analysis of the entity being sensed can be completed. FIG. 1 depicts the basic principle of SAW based bio/chemical sensors employing the mass loading scheme.

Using a combination of IC compatible technologies, such as Si micromachining, thin film deposition, bio/chemical layer growth, integrated electronics, smart structures and systems can be realized. Considering the advantages that CMOS technology provides along with the ever-developing CMOS compatible MEMS processes, the SAW technology performance can be improved significantly. Therefore, an array of SAW delay lines were designed and fabricated through a regular CMOS process sequence, characterized and post-processed using widely used MEMS techniques.

II. Design

Figure 2:
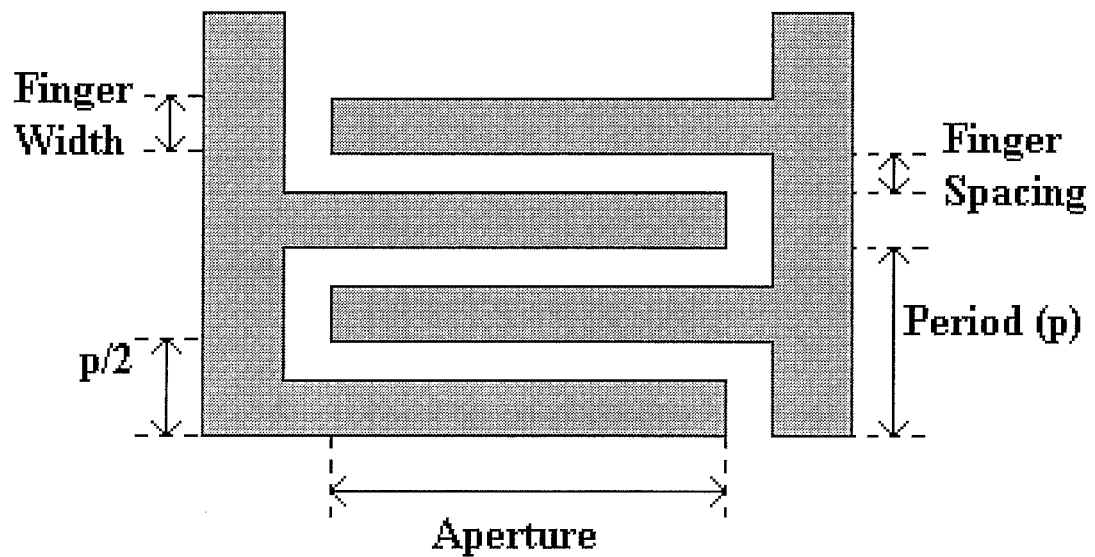
FIG. 2. The major design dimensions of the IDT fingers.

The mass sensitivities of different acoustic devices are related to structure geometry, resonant center frequency, and electromechanical coupling. In order to explore all of these design parameters, an array of SAW devices were designed. FIG. 2 depicts the important dimensions of the devices that were fabricated. Four devices on the dies were tested with finger width of 2.40 μm, finger spacing of 2.40 μm and a period of 9.60 μm. The apertures were picked to be 54.80 μm (device 1 and 2), 502.80 μm and 244.80 μm. 24 and 32 finger pairs were used with delay line lengths of 288 μm and 384 μm. Note that all of these devices were designed on the same die which is a 2.2 mm by 2.2 mm tiny chip. The design was fabricated in AMI 1.5 μm 2 metal, 2 poly process through MOSIS. In order to comply with the design rules for this technology, the minimum finger spacing for the IDTs is limited to 2.4 μm. This limitation is due to the minimum metal to metal spacing for the aforementioned technology.

The most important specification for SAW device design is the center frequency, which is determined by the period of the IDT fingers and the acoustic velocity of the piezoelectric material.

The governing equation that determines the operation frequency is $$vSAW = \lambda \times fc \quad (1)$$

λ: the wavelength at fc, determined by the periodicity of the IDT.
fc: the center frequency of the device
vSAW: the velocity of the SAW
For the case of devices that were tested $$\lambda = p = \text{finger width} \times 4 = 2.4 \ \mu m \times 4 = 9.6 \ \mu m \quad (2)$$

Based on tabulated data and calculations for the corresponding design dimensions vSAW for ZnO is 3820 m/s. This translates into a center frequency of $$fc = 3820 \ m/s / 9.6 \ \mu m = 397.916 \ MHz \quad (3)$$

III. SAW Fabrication Sequence and Results

The conventional SAW devices are typically built by depositing a piezoelectric material (quartz, lithium tantalite, lithium niobate, zinc oxide) on a substrate and patterning the IDTs on top of the piezoelectric film as depicted in FIG. 1. This sequence of fabrication does not comply with any commercially available CMOS process as it requires an extra step to deposit the piezoelectric material. It has been reported that enhanced electromechanical coupling is theoretically possible using piezoelectric films overlaying interdigital metal electrodes. Therefore, IDT under the piezoelectric material idea is employed for this work. By depositing the piezoelectric material on top of the IDTs as a post processing step, the CMOS process is not disturbed.

For device stability as a function of temperature it is essential that the temperature coefficient of delay (TCD) be as small as possible. The slope of the TCD as a function of temperature for SAW substrates is mainly negative, so that an increase in temperature will cause a downward shift in IDT center frequency and vice-versa. Due to this strong temperature dependence of the device performance and for precise control of the temperature to study the effects of temperature on the mass sensitive layer and the analyte of interest, a novel heater design is developed. For the heater elements n-well was picked as the resistive layer. The n-well layer has a TCR of 0.5-0.75%/K, which is the highest among various CMOS process layers. Moreover, n-well provides an embedded heater structure that can directly control the temperature of the substrate and the mass sensitive area without causing any disturbance on the SAW delay line path or the IDT finger design as in the case of other candidate layers (e.g. polysilicon, metal) for resistive heating.

The major distortions in the transfer characteristics of SAW devices occur due to interference of the reflected waves and the triple transit effect. In Rayleigh wave devices, acoustic absorbers were shown to be effective against the reflections. They consist of soft materials located on the surface, at the edges of the device. In order to investigate the performance of the SiO2 in reflecting or attenuating acoustic waves, an absorber structure was designed from stacking CMOS layers of metal1, metal2 and polysilicon. By stacking these dummy strips, a surface higher than the IDT level was created which is investigated for attenuating or reflecting the acoustic waves. FIG. 3 depicts the side view of the design after CMOS process was completed and before any post processing was carried out.

A. Step 1: Removal of Oxides

After the chips are fabricated, they are covered with the overglass protection and the dielectrics (SiO2) over and underneath the metal and poly layers. The first step in the fabrication is RIE (Reactive Ion Etch). This step has been developed, examined, and characterized previously. Note that AMI 1.5 μm process contains only two metal layers, one of which is already being used as IDTs in this run and the second metal layer will be used in the absorber structures for two main purposes. 1) To increase the height of the absorber compared to the height of the IDTs 2) To act as a mask layer that protects the oxide, which is built up under this layer. The RIE etches the dielectric that is not covered with aluminum, including field oxide, overglass, and intermetal dielectrics. The dies that were fabricated through MOSIS were RIE etched through MEMS-Exchange. The etching was carried out in a Plasma Therm 72 RIE equipment under 40 mTorr pressure.

The etch rate is 250 Å/min. The depth of the total oxide removed by the etch process is 1.5 μm. After the RIE step is completed, three major areas are defined on the surface. The absorbers, the IDTS (both of which are expected to retain their dielectric layers underneath) and exposed Si, which lay between the IDTs and the area that will define the delay line. FIG. 4.a. depicts the side-view of the die after the RIE and FIG. 4.b. is an SEM of the device after RIE.

B. Step 2: Sputtering of ZnO

ZnO finds wide applications in SAW devices due to its strong piezoelectric effect among non ferroelectric materials. A variety of deposition techniques were used for the growth of ZnO on various substrates. Among them sputtering is considered to be the most favorable one as it is possible to obtain well oriented and uniform ZnO films. Therefore, RF magnetron sputtering was the choice of deposition in our work.

By maskless sputtering from the front, the ZnO covers the entire surface including the IDT fingers and the exposed Si. This inevitably creates bulks of ZnO layers between the IDT fingers. FIG. 4.c shows the side-view of the die after the ZnO deposition. Sputter deposition of zinc oxide shows superior properties over other deposition methods, but the quality of the sputtered film and the growth constitutes a major interest in SAW related applications. The ZnO was deposited on the previously etched dies through MEMS-Exchange. The targeted thickness was 3.0 μm and the measured film thickness variation was (+/-%) 13.1. Argon and oxygen were used with a set-up time of 180 min in an MRC Sputter at 200° C.

Figure 5A:
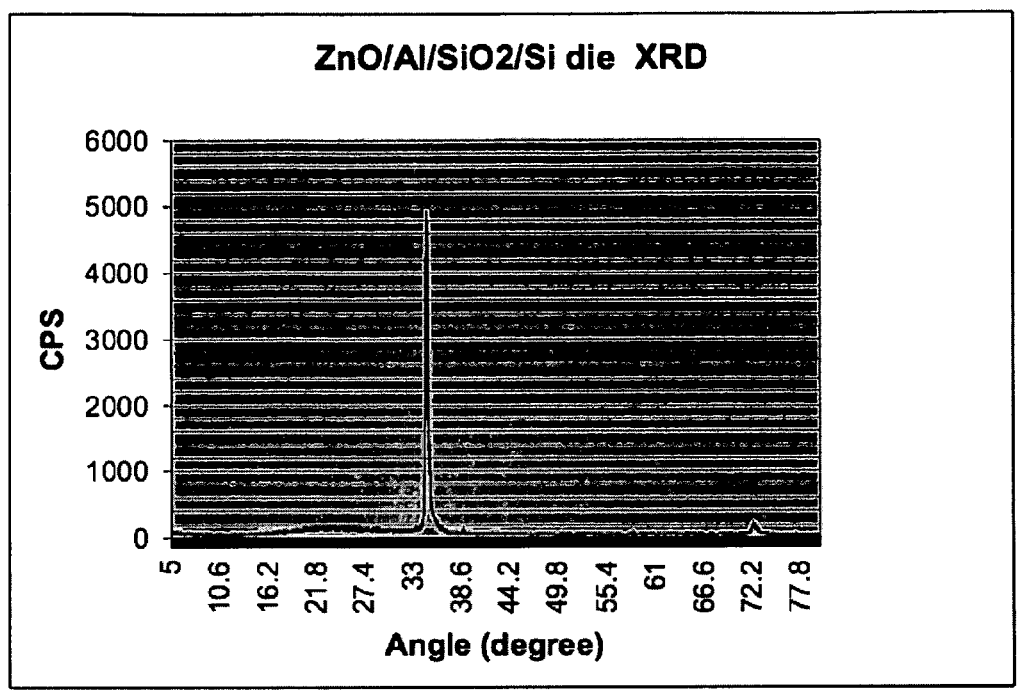
FIG. 5 (a) The $2\theta_i$ scan of 2.6 μm thick ZnO layer on top of Al—$SiO_2$—Si layered structure (b) SAW IDT edge profile of the last two IDT and the delay line (c) Depth measurements and the profile diagram for the IDT edge.
Figure 5B:
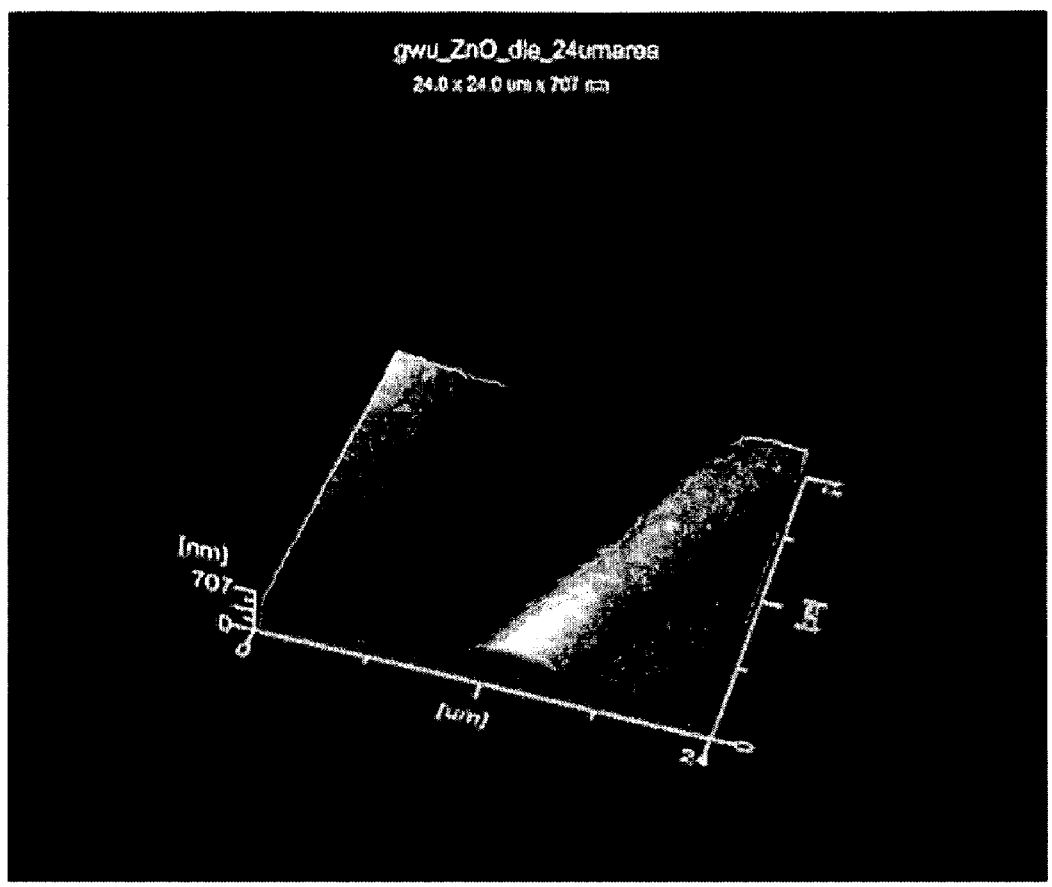
Figure 5C:
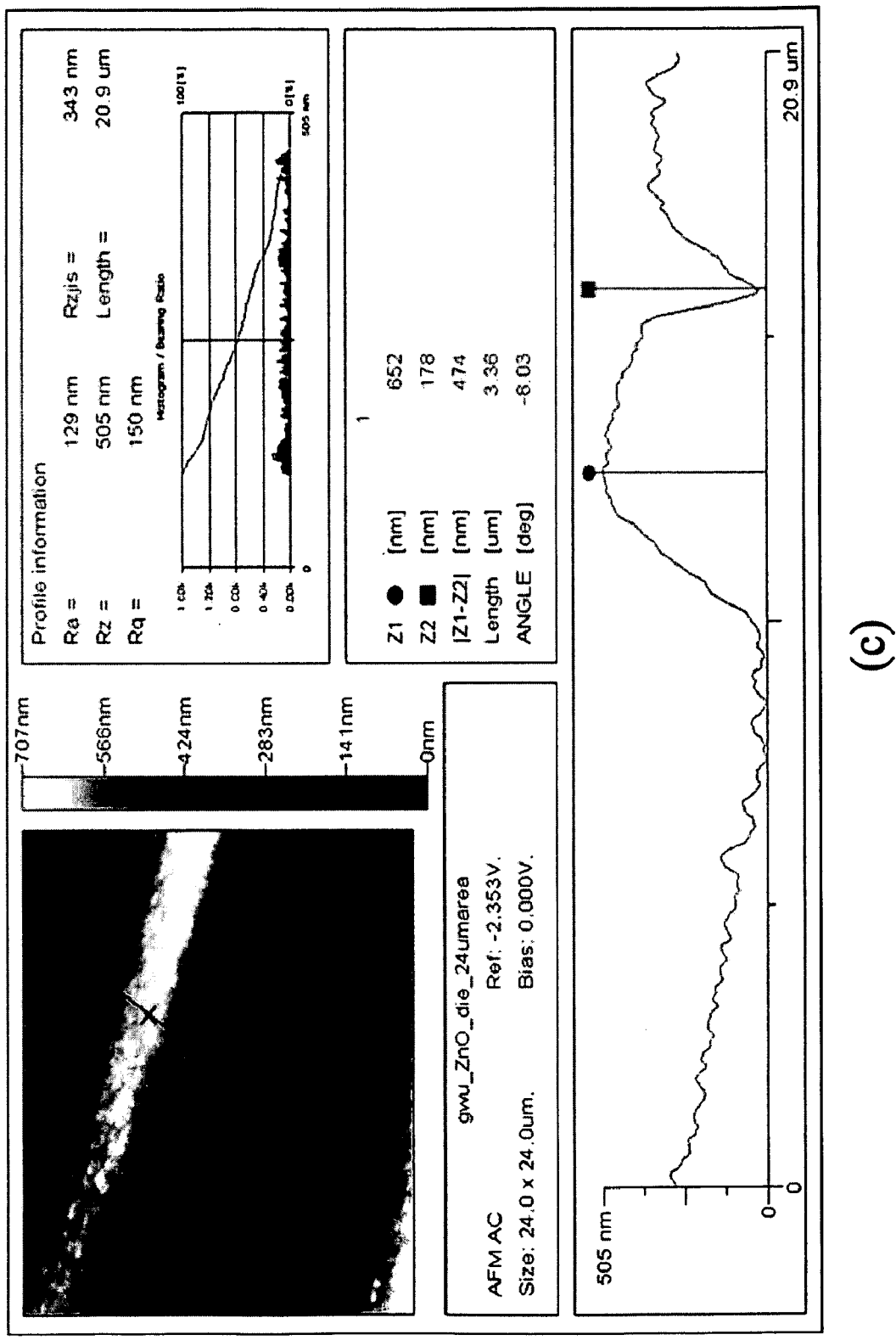

The surface morphology, roughness and the crystal orientation of the sputtered ZnO are subject of interest. Therefore, a thorough characterization of the sputtered films is required. The ZnO covered samples are analyzed for the crystal orientation in Scintag XRD 1000. For comparative analysis, 2θi scans of a dummy die (Si—ZnO) and a patterned die (Si—SiO2-Al—ZnO) were carried out. As it can be seen from FIG. 5.a, the ZnO shows its peak at 2θi= 34.721, which agrees with the tabulated data in the literature for (002) 2θi=34.421. It also has a peak at 2θi=73, which corresponds to its listed peak at 2θi=72.560 for (004). In order to obtain information regarding the surface roughness and grain size JOEL High Vacuum Integrated STM/AFM/JSPM-5200 was utilized. The multilayered (Si—SiO2-Al—ZnO) dies were characterized. FIG. 5.b,c shows the results.

C. Step 3: Patterning of the Pad Frame/ZnO Etching

After the ZnO deposition the entire die is covered with the sputtered ZnO. In order to access the pads for bonding a last step of lithography and etching are required. The entire die area is 2.2 mm×2.2 mm and the pads are 100 μm×100 μm. A simple shadow mask idea was employed for the etching step. The mask was constructed by using a square Si piece of size 2×2 mm. The major problem encountered during the patterning was the photoresist build up on the edges of the die. Thickness measurements showed a 2-4 μm photoresist buildup on the pad frame region when the thickness on the areas closer to the center of dies were measured to be 1 μm. In order to completely remove the photoresist build up covering the pad frame, a two step process was carried out. In the first step, Shipley 1818 2:1 thinner was spun for 40 sec at 5000 rpm and the samples were exposed for 20 sec. Then a 2 min development in 5:1 Developer was applied. In the second step, the same exposure time and development time was used to remove the excessive photoresist.

In general, ZnO is attacked by all common acids and bases. In order to achieve smooth etch profiles and minimize the undercutting, the etching process should be slowed. Therefore, a very dilute solution of two acids was used. The most common acids that are listed in the literature are acetic, hydrochloric and phosphoric acids. A solution of $H_3PO_4$: $CH_3COOH$:DI-$H_2O$ with 1:1:150 was used for the etching.

2.6 μm thick ZnO was etched completely in 4 min, which translates into 648 Å/min etch rate. Once the final step of post processing was completed, the dies were bonded on a DIP-40 package for electrical testing. The major subjects of interest for performance analysis of SAW devices are the transmission coefficient and the reflection coefficient versus frequency. HP 8712ET, 300 kHz-1300 MHz, RF Network Analyzer was used for this purpose. A through-cable calibration was carried out in order to measure and compensate for the losses and errors due to the connector and cable irregularities.

S11 (reflection) and S21 (transmission) coefficient versus frequency is shown in FIGS. 6.a and 6.b respectively. The center frequency of the delay line agrees closely with the calculated value.

Thus, a test chip that contains an array of SAW delay lines were designed and fabricated in AMI 1.5 µm 2 metal, 2 poly process. A unique, three step, maskless post processing sequence was developed. Complete characterization of the two etching steps and piezoelectric film was carried out. The transfer characteristics show a maximum transmission and minimum reflection at 392.5 MHz with an insertion loss of −4.83 dB. The 3 dB bandwidth was measured to be 19.25 MHz which agrees closely with the calculated value of 14.575 MHz. The results demonstrate that it is possible to design and fabricate SAW based sensors with comparable performance to conventional devices by using any commercially available CMOS technology.

CMOS Process Sequence

CMOS fabrication technology is well established and requires that both n-channel (nMOS) and p-channel (pMOS) transistors be built on the same chip substrate. To accommodate both nMOS and pMOS devices, special regions must be created in which the semiconductor type is opposite to the substrate type. These regions are called wells or tubs. A p-well is created in an n-type substrate or, alternatively, an n-well is created in a p-type substrate. In the simple n-well CMOS fabrication technology presented, the nMOS transistor is created in the p-type substrate, and the pMOS transistor is created in the n-well, which is built-in into the p-type substrate. In the twin-tub CMOS technology, additional tubs of the same type as the substrate can also be created for device optimization.

The simplified process sequence for the fabrication of CMOS integrated circuits on a p-type silicon substrate starts with the creation of the n-well regions for pMOS transistors, by impurity implantation into the substrate. Then, a thick oxide is grown in the regions surrounding the nMOS and pMOS active regions. The thin gate oxide is subsequently grown on the surface through thermal oxidation. These steps are followed by the creation of n+ and p+ regions (source, drain and channel-stop implants) and by final metallization (creation of metal interconnects).

An integrated circuit (IC) is a circuit comprised of elements such as transistors, resistors and capacitors fabricated in a single piece of semiconducting material, usually silicon or gallium arsenide. As used herein, "integrated circuit" not only refers to the common definition but also to highly integrated structures including, for example:
1) multichip modules where several IC's and other circuit elements including molecular target probes may be combined compactly on a polymer, quartz, glass, sliver, ceramic or other substrates. In some cases, one IC may be the substrate with other components, such as photodiodes or LEDs mounted on it;
2) Hybrid microcircuits where one or more IC's and other circuit elements are mounted on or several substrate(s); and,
3) Other compact electromechanical arrangements of a circuit comprising primarily one but possibly more IC's and other electronic components and microelectromechanised systems (MEMs).

Surface Acoustic Wave Resonators

There has always been motivation to fully integrate the wireless transceiver. Surface acoustic wave (SAW) resonators have commonly been used as the local oscillator (LO) which is one of the basic building blocks of the RF receiver heterodyne architecture and is currently the major stumbling block for complete integration of RF receivers. Due to the structure of the SAW devices that require fabrication of metallized interdigital transducers on piezoelectric crystals, the SAW resonators are difficult to implement in CMOS and are usually realized as discrete off-chip components. Efforts to integrate surface acoustic wave filters on silicon substrates have been previously implemented by Visser, Vellekoop and Zeijl while the monolithic integration of SAW devices on GaAs has been implemented by Baca of Sandia National Labs. The operating frequency of a surface acoustic wave resonator is determined by the periodic distance of its interdigitated transducer (IDT) fingers, $\lambda$, which are placed on piezoelectric material. Unlike bulk-wave crystal resonators, whose frequency of operation is determined by the thickness of the piezoelectric material, surface acoustic wave resonators have a more area efficient structure since its frequency of operation is determined by the spacing between the IDTs and thus is only limited by the resolution of the fabrication process. The utilization of surface waves, instead of bulk-waves, makes the process of integration with the present integrated circuit fabrication techniques more feasible since it eliminates the necessity of having a thick piezoelectric layer sandwiched between two metal layers.

In the present invention, implementation of surface acoustic wave resonators using the standard CMOS fabrication technology with additional post-processing techniques is provided. The fact that the fabrication process of this SAW resonator is highly compatible with current integrated circuit processing techniques makes it extremely desirable since it is not only cost-effective, but also allows the resonator features to be less prone to manufacturing defects due to the maturity of CMOS technology. In this design, the SAW resonator utilized the minimum feature sizes possible in the available 0.6 micron AMI CMOS process to realize a 1.15 GHz surface acoustic wave resonator.

The fabricated CMOS resonators were measured, and modeled as a two-port electrical network through analog circuit synthesis. This model was used as a basis for simulation in Cadence to design a Pierce oscillator. The Pierce amplifier was designed on a separate CMOS chip. When connected together, the Pierce amplifier and SAW resonator realize an oscillator capable of synthesizing a frequency of 1.15 GHz. By having both the resonator and the oscillator integrated on the same CMOS chip, a fully monolithic frequency synthesizer is realized.

II. CMOS Surface Acoustic Wave Resonators: Design and Equivalent Circuit Model

1A. SAW Resonator Design

Figure 7A:
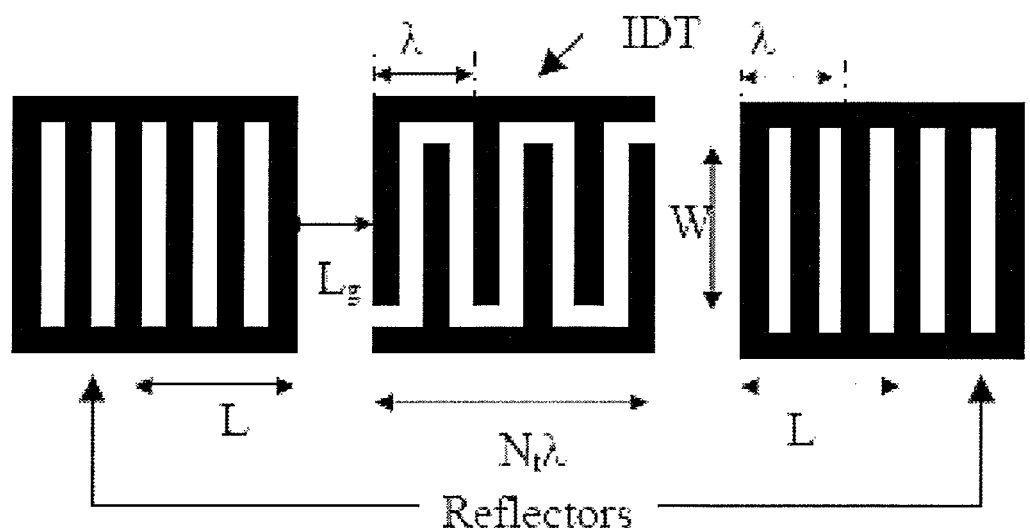
FIG. 7(a) shows the SAW resonator design parameters of a 1-port resonator.

The SAW resonator design consists of input or output IDTs flanked by a bank of reflectors on both sides. Refer to FIG. 7(a) which illustrates the important design parameters of a 1-port resonator. The key design parameter is $\lambda$, or the periodic distance between two interdigitated fingers, which determines the frequency of the resonator, using $v=f\lambda$, where v is the velocity of the acoustic wave in the piezoelectric material and f is the resonant frequency. In this design run, $\lambda$ was chosen to be four times the minimum metal2 size of this technology or 3.6 micron. The modeling equations for SAW resonators, which involve rigorous computations of transmission matrices, will not be discussed in detail in this paper but the basic methodology of designing the SAW resonators and its accompanying oscillator circuit is outlined here.

The main design parameter that needs to be chosen is M or the number of reflectors. An array of reflectors is required since each electrode only produces reflectivity, r of approximately 0.08. The equation for reflectivity was derived based on the theory of reflection in transmission lines, and is given in (1A), where $\eta$ is the metallization ratio of the IDT, Z is the characteristic impedance of the region under the reflector, $\Delta Z$ is the difference of characteristic impedance between the free region and the region under the reflector, and finally, $f_r$ is the resonance frequency.

$$r = j\frac{\Delta Z}{Z}\sin\left(\eta\pi\frac{f}{f_r}\right) \tag{1A}$$

$$\Gamma \sim \tanh(M) \tag{2A}$$

$$L = 1/(4|r|) \tag{3A}$$

The array reflectivity, $\Gamma$ can also be approximated as (2A) and the number of reflectors was chosen to optimize area while maintaining array reflectivity to be close to 1. The effective center of reflection, or the line where the surface waves are assumed to be totally reflected is denoted by L is expressed as (3A) where r is the reflectivity of each electrode. MATLAB simulations of (1A), (2A) and (3A) using ZnO thin film material properties were performed to obtain the optimum number of reflectors which was found to be 125 for this design. The total effective length of a round trip in the cavity must be an integer number of λ. Other important design parameters are the distance between the reflectors and the input transducers Lg, the number of IDTs or $N_t$ and the width of the transducers or W. Thirty-two different designs of SAW resonators were first fabricated on piezoelectric substrates such as lithium niobium substrates to evaluate the performance of the fabricated designs. Four resonators with the best performance characteristics were then chosen and scaled to fit the 0.6 um CMOS in this design run.

1B. Equivalent Circuit Model

Figure 7B:
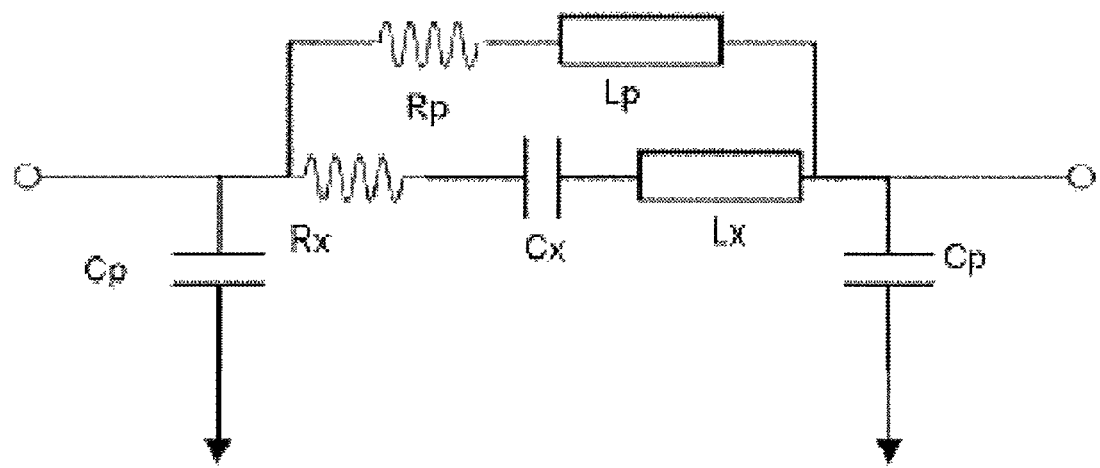
FIG. 7(b) shows an Equivalent circuit model of a two-port SAW resonator.
Figure 8A:
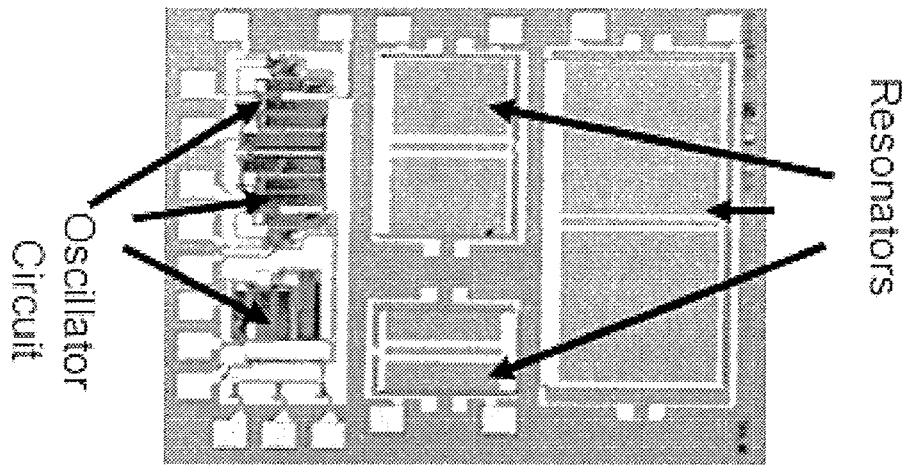
FIG. 8(a) shows Chip B: CMOS Oscillator Die Photo.
Figure 8B:
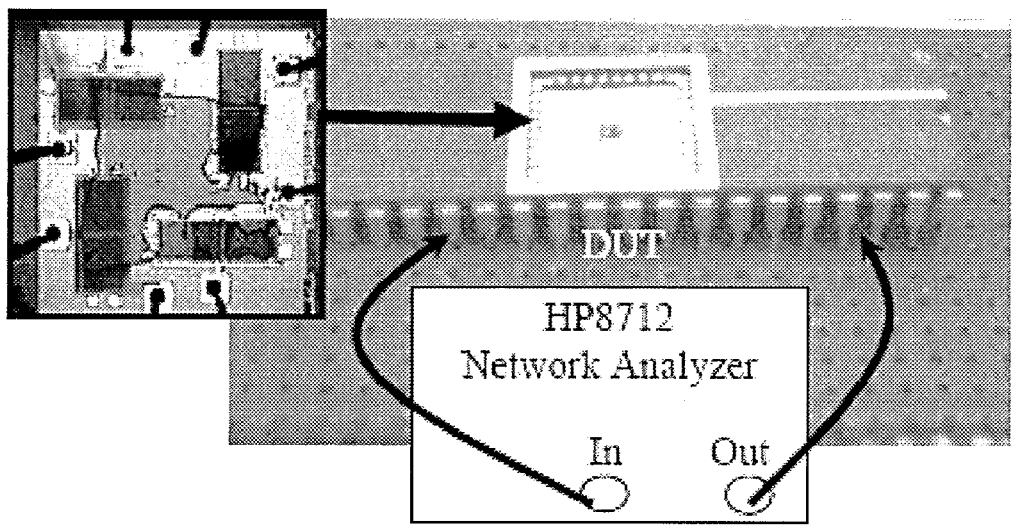
FIG. 8(b) Experimental Setup: clockwise from left: Bonded Die. Middle: Device under test (DUT) in DIP 40 package. Bottom: DUT connected to HP8712 network analyzer.
Figure 8C:
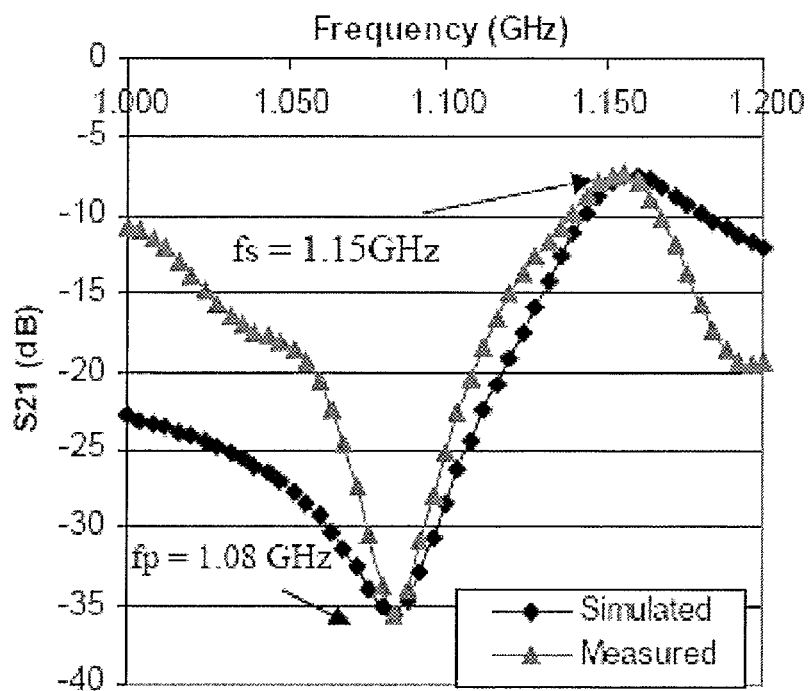
FIG. 8(c) shows the Measured and Simulated S21 Transmission Characteristics of Resonator 4.

The equivalent circuit model of a two-port SAW resonator was developed using analog circuit synthesis based on the S21 frequency measurements made on the fabricated CMOS resonators. The SAW resonator has transmission characteristics similar to a series LCR circuit, where the series resonant frequency is generated by both $L_x$ and $C_x$. The initial values for the LCR circuit were calculated using the resonator design equations based on the reflectivity of each metal strip and number of reflectors. This basic LCR circuit was then modified based on curve fitting, where the simulated values were compared with the experimental measurements. Several circuit topologies were implemented an least squares method was used to choose the circuit, which produced the best fit. The final circuit topology that produced the best fit is shown in FIG. 7(b), where it consists of Rx, Cx and Lx which are motional resistance, capacitance and inductance connected in parallel with Lp and Rp. The input and output ports are connected with parasitic capacitances Cp to ground. The circuit's S21 scattering parameters analysis simulations were performed using Cadence SpectreRF where the input and output ports were terminated with 50 Ohms. Comparison between the measured and simulated equivalent circuit model is shown in FIG. 8(c). The best fitting curve was found to have the values of Lx=1 uH, Rx=120 Ohms, Cx=19 fF, Lp=132.8 nH, and Cp=10 fF.

III. Fabrication

Perhaps the most important highlight of this SAW resonator design is that the SAW resonator IDT's can be implemented using standard CMOS technology. This allows the resonator features to be realized in the minimum sizes available in the AMI 0.6 micron CMOS process, making them not only less susceptible to manufacturing defects but also less expensive compared to when fabricated as micromachined MEMS structures. The resonator features were implemented as 0.9 micron wide metal2 lines which are able to realize ultra-high frequency, 1.15 GHz resonators.

Figure 7C:
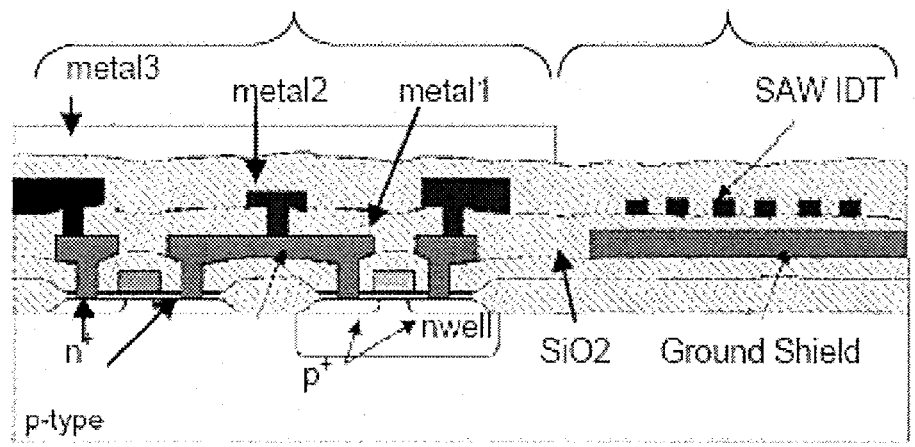
FIG. 7(c) is a cross section of a CMOS SAW oscillator before post-processing.

The SAW CMOS post fabrication sequence is similar to the CMOS SAW delay line, with several important distinctions, namely the presence of the aluminum ground metal1 shield which was placed to eliminate electromagnetic feed-through. The other major difference is the presence of the oscillator circuit which is also placed on the same die and protected by a grounded metal layer as shown in Chip B shown in FIG. 7(c) and FIG. 8(a).

Once the standard CMOS fabrication sequence is completed, the first post-processing step involves releasing the SAW IDTs from the insulating SiO2 layer using reactive ion etch (RIE). The next step is ZnO deposition, which was sputtered on the resonators. The final post-processing step involves wet-etching the ZnO to uncover the resonators' pads.

Figure 7D:
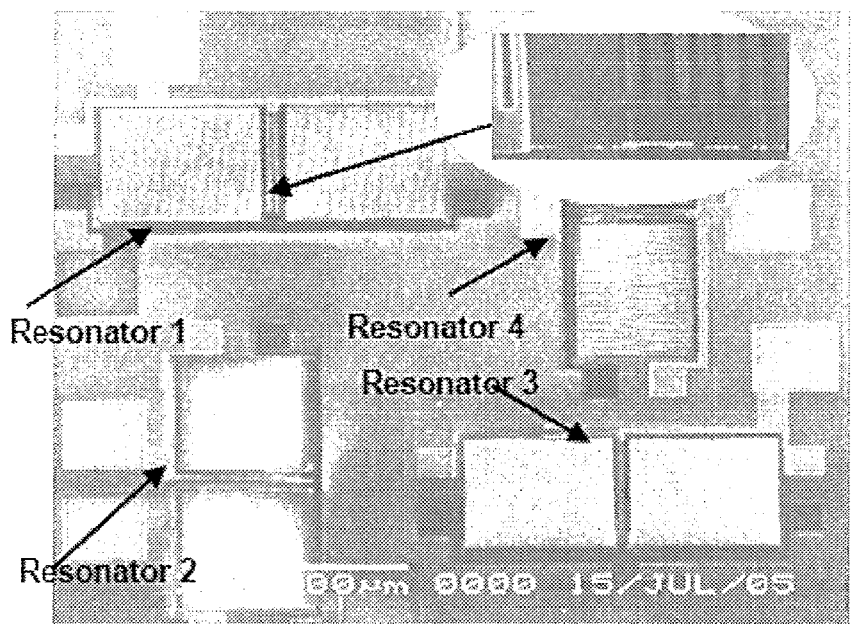
FIG. 7(d) shows Chip A: a SEM micrograph of 0.6 micron CMOS resonator.

Two separate CMOS chips had been designed. The first chip shown in FIG. 7(d) (Chip A) consists of four CMOS SAW resonators was fabricated and characterized prior to the design of the second chip. Chip B which consists of three resonators and the Pierce oscillator circuit is shown in FIG. 8(a). Chip A was designed to characterize the ultra high frequency resonator of frequencies in the range of 900 MHz to 1.2 GHz. Chip B was implemented as a proof of concept that the post-processing techniques of the SAW resonator do not adversely affect the amplifier circuit.

IV. Experimental Results and Discussion

Once the post-processing steps have been completed, the die was bonded and packaged in a DIP40 chip package to facilitate measurements. The bonded device was measured using a HP8712 network analyzer and its experimental setup is shown in FIG. 8(b). The S21 measurements made on the 0.6 micron CMOS SAW resonators produced the parallel resonance frequency, fp of 1.084 GHz and the series resonance frequency, fs of 1.156 GHz as shown in FIG. 8(c). Based on the measurements, the parallel Q was calculated to be 90.33 and series Q was calculated to be 36.125. The measured Q was not as high as expected since the die was overetched and some parts of the resonator was not completely covered as shown in the bonded die image of FIG. 8(b). The acoustic wave velocity of ZnO calculated from the measured curve was found to be 4140 m/s.

V. Oscillator Design and Simulation

Figure 9A:
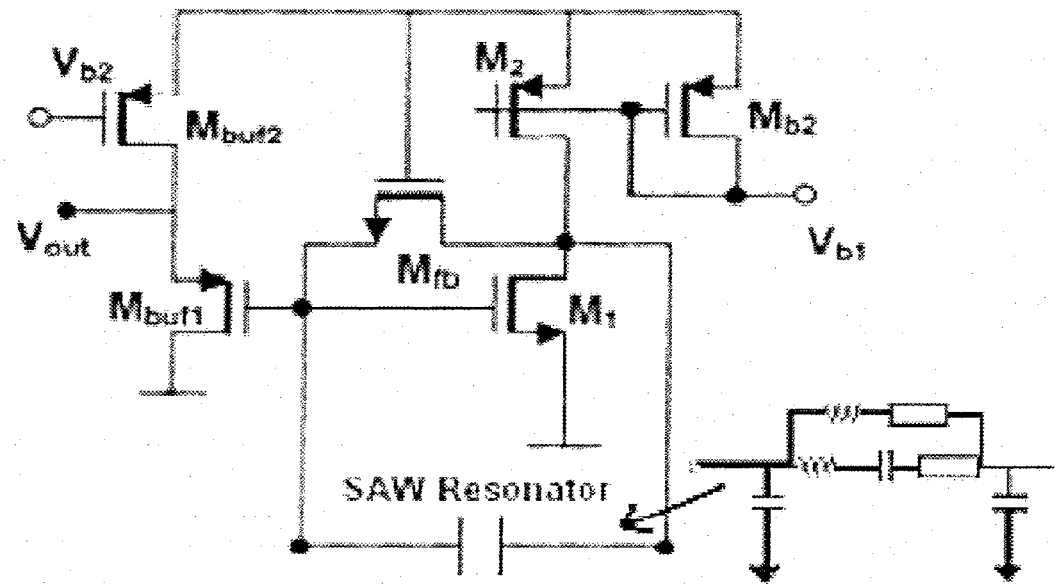
FIG. 9(a) is a SAW Resonator and Pierce Oscillator Schematic.

To operate as a local oscillator, the SAW resonator is connected to a Pierce oscillator at the gate and drain of M1 as shown in FIG. 9(a). This three-point oscillator topology was previously implemented using an FBAR oscillator by Otis, and was chosen firstly since it utilizes the current source, M2 to provide the necessary biasing current to M1, as the SAW resonator does not pass any DC current. Secondly, it also provides excellent phase noise characteristics. Mfb, operates as a resistor which provides bias to the gate of M1.

$$A_{CL} = g_m R_p (C_{p1}/C_{p2}) \tag{4A}$$

Figure 9:
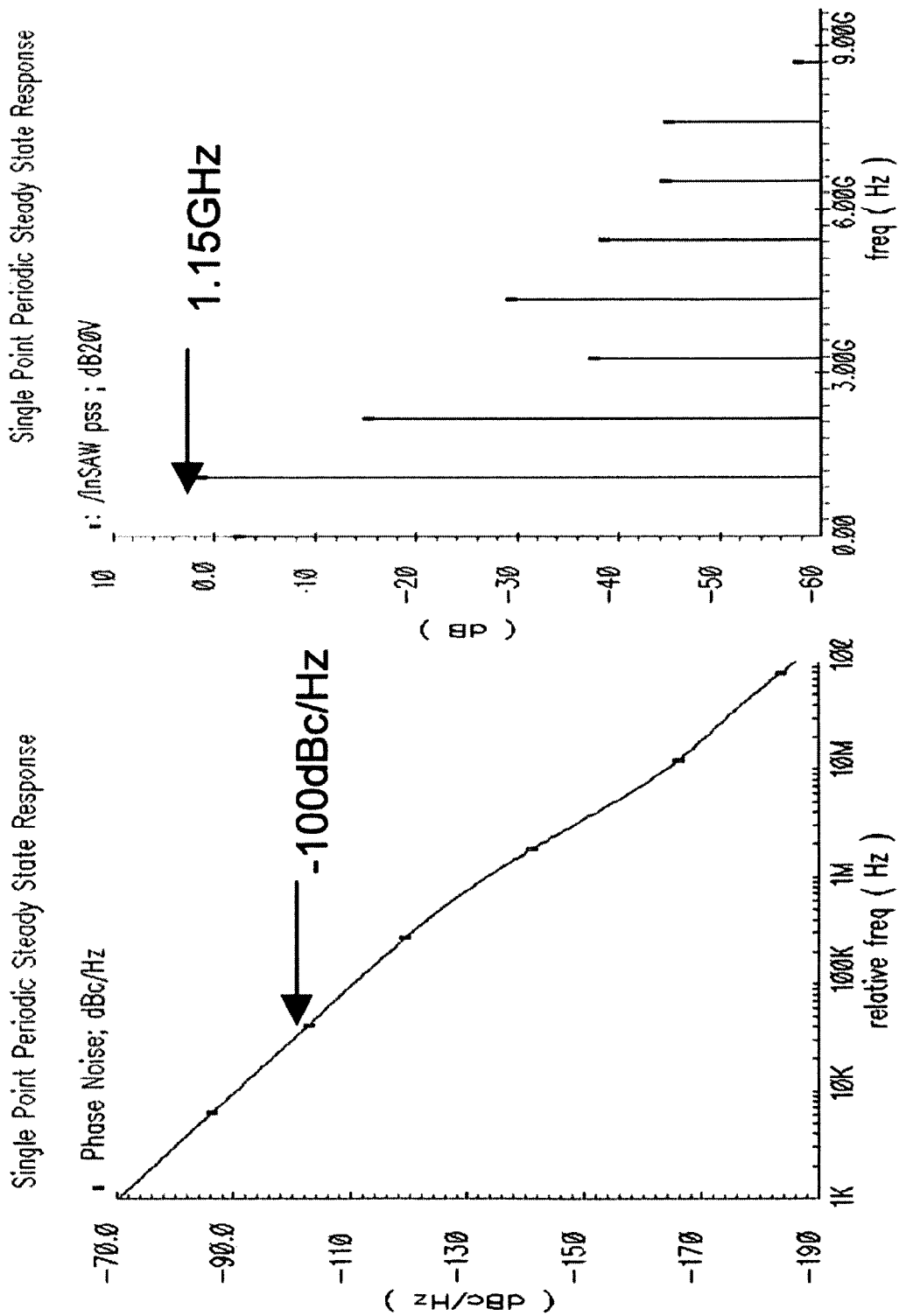
FIG. 9 (b) shows the Phase noise and steady-state analysis of SAW Oscillator.

To ensure oscillation, the loop gain, $A_{CL}$ has to be greater than 1 and the phase shift should be equal to 0. Based on (4A), the size of M1 is adjusted to provide the necessary transconductance to counteract $R_p$, where $R_p$ is the parallel reflected motional resistance at the gate of M1. For this design Cp1=Cp2 which also maximizes the open loop gain. The transistors were sized as follows, M1=4.8 m/1.6 u, $M_{fb}$=4 u/872 u, M2=9.6 m/1.2 u. The phase noise performance and steady-state analysis of the oscillator circuit was simulated using Cadence SpectreRF to obtain its fundamental beat frequency of 1.154 GHz are shown in FIG. 9 b.

Accordingly, the design, implementation and measurements of a CMOS SAW resonator is provided. The SAW resonators were fabricated using standard AMI 0.6 micron CMOS technology with some additional post-processing steps. Upon completion, the SAW resonators were characterized and found to have a resonant frequency of 1.15 GHz and its equivalent circuit model was developed based on these measurements. This model was used to design and simulate a Pierce 1 GHz oscillator.

Chemical Sensors

During the manufacture of analyte detection chips, a sensor material is placed on the substrate. This sensor material may be deposited, coated, or otherwise applied on the substrate. In one embodiment, the sensor material is any material which provides an electrical response to an analyte. For example, an electrical response may be quantified in terms of impedance (Z), resistance (R), inductance (L), capacitance (C), or other electrical property. In an embodiment, the sensor material may be a polymer. The material may be organic, or inorganic in other embodiments. Further, the sensor material may consist of regions of a nonconductive organic material and a conductive material. In other embodiments, the sensor material may be insulating organic films that act as capacitors or composite films that act as inductors. A more detailed description of some sensor materials and their properties is discussed in U.S. Pat. No. 5,571,401. However, the present invention is not limited to the sensor materials in U.S. Pat. No. 5,571,401 since other materials may also be used.

In a specific embodiment of the present invention, the sensor technology may involve a series of conductive polymeric composite vapor sensors. The presence of an analyte may be detected through a change in, for example, the electrical resistance of a chemically sensitive carbon-based resistor. As discussed above, changes in electrical properties other than resistance may also be used; these include the evaluation of capacitive and inductance changes.

Further, the sensor material may be composed of conductor and insulator composites. This material may be placed on the substrate in a film. The organic nonconducting polymer of the composite absorbs the analyte (which may be a vapor). This induces a change in the electrical properties of the sensor material. The sensor material may also undergo physical changes such as swelling. When the analyte is removed, any changes in the electrical properties reverse. For example, the resistance, capacitance, and inductance may return to their original value. Any physical changes would also reverse. The response of these types of sensors are reversible over multiple analyte exposures as well as reproducible over a large number of trials under a variety of ambient atmospheric conditions. Therefore, a device fabricated using these types of sensor materials would have a relatively long service life.

In the case of using a composite such a nonconducting polymer and carbon black, the sensor material will be temperature sensitive. When using temperature-sensitive sensors, the sensor should be kept at a relatively constant temperature to provide relatively consistent results. For example, a temperature such as about 5 degrees C. above the ambient should provide good results. Further, extremely high temperatures, say, above about 100 degrees C., should be avoided since these temperatures would destroy the polymer sensor material or rapidly decrease its service life. For this reason, it is not expected that nonconducting polymer materials are to be used in the specialized environment of extreme high temperatures, say, from about 300 degrees C. to about 400 degrees C. or even higher. The polymer sensor materials will be usable in the normal temperature ranges from about 0 degrees C. to about 100 degrees C.

Using a conductor and insulator composite for the sensor material permits a very broad, diverse collection of sensor materials. For example, any conducting element including carbon blacks, metallic colloids, or organic conducting polymers, and combinations of these, may be used as the conductive phase of the sensors. Any organic material may be used as the insulating phase of the sensors. Furthermore, an advantage of these types of sensor materials is that they do not have the stability limitations of conducting organic polymeric materials. A conductor and insulator composite also does not suffer the limitations from the types of substituents or restrictions on the ranges of swelling variations that can be obtained from backbone modification of pure organic conducting polymers.

After processing of a substrate or wafer is complete, the wafer is tested to determine the number and location of the "good die." The percentage of good die on one wafer compared to the total number of die on the wafer is referred to as the "yield." Individual analyte detection dies are separated by sawing along the scribe lines. The analyte detection dies are then packaged, and may be further tested to ensure their proper operation. These dies may be packaged in a variety of packaging material including ceramic, epoxy, plastic, glass, and many others. Packaged analyte detection die may very much resemble packaged integrated circuit chips. For some types of applications, nonporous, nonreactive materials like ceramic may be used.

In one embodiment, the sensor material is deposited or applied at the wafer level, before individual dies are separated. In other embodiments, the sensor material is applied after the dies are separated.

Biological Sensors

Surface acoustic wave devices as biosensors are also well suited for the detection of biological agents. Positioning a receptor between IDT fingers to induce a phase shift or within IDT fingers to induce a frequency shift allows for electronic detection of bioagents. These devices have the dual advantages of high sensitivity, down to picograms/cm2, and high specificity, conferred by biological receptors such as antibodies, peptides, and nucleic acids. Detection of bacteria, viral particles, and proteins has been shown with these types of sensors. Handheld biodetection systems incorporating these microsensors are contemplated as within the scope of the invention.

The surface acoustic wave biosensor arrangements may be used for real time sensing and for quantifying the levels of bacteria, e.g. *Escherichia coli*.

Many monoclonal antibodies with high affinity and specificity for particular bacteria are available from commercial sources as well as the American Type Culture Collection (ATCC). For example, one of these antibodies, the ATCC HB-8178 antibody, may bind with the *E. Coli* pilus with high specificity and affinity. Any known coupling chemistry may be used for binding the monoclonal antibody to the sensor chip surface.

It may also important to optimize the chemical linking of the antibody, as well as the loading density. Independent fluorescence assays of the antibody density on the chip may be done using fluorescence labeled anti-IgG. The chip may be incubated in phosphate buffered saline with fluorescein labeled anti-IgG, and may then be washed with a buffer solution of increasing ionic strength to dislodge unbound antibody. The chip may then be scanned using a Perkin Elmer LS50B fluorescence spectrophotometer, and the bound antibody density may be calculated using FL-Winlab software, which may also calculate various parameters (such as, for example, the statistical variability observed in the surface loading between regions on the chip sample surface). This technique may be used to determine which of the coupling chemistries yields the best loading of antibodies.

Biological detection may include detecting of smaller molecular weight molecules as well as larger protein molecules, amino acids, and nucleic acids.

Current generated per analyte molecule bound to the biosensor surface may be compared to the response obtained from control. Analyzing the differences in the biosensor response may be useful for improving the chemistry and spatial properties of the biosensor arrangement to enhance its performance against the analyte of interest.

There are a number of U.S. patents which describe integration of a biosensor chip into a biosensor device, including U.S. Pat. Nos. 6,937,052, 6,743,581, 6,657,269, and 6,448,064, all incorporated herein in their entirety. Other U.S. patents describe the use for detection of a chemical, including U.S. Pat. Nos. 6,627,154, and 6,495,892, incorporated herein in their entirety.

SAW-Based Chemical Sensors

SAW devices are extremely sensitive to tiny mass changes, detecting 100 pg/cm$^2$—less than 1% of a monolayer of carbon atoms. When coated with a chemically selective thin film, the SAW device is rendered sensitive to chemicals that interact with the film. Sensors based on surface acoustic wave (SAW) devices are being developed to detect a wide range of chemicals. The SAW device is an extremely sensitive gravimetric detector that can be coated with a film to collect chemical species of interest. Based on these devices, sensor systems have been developed that can detect trace (ppm to ppb) levels of airborne contaminants. Applications include weapon state-of-health, environ-mental, and non-proliferation monitoring.

Chemical species that have been distinguished as capable of detection up to 96% accuracy include the general categories of organophosphonate (DIMP, DMMP); chlorinated hydrocarbon ($CCl_4$, TCE); ketone (acetone, MEK); alcohol (methanol, n-propanol, pinacolyl alcohol); aromatic hydrocarbon (benzene, toluene), saturated hydrocarbon (n-hexane, cyclohexane, i-octane); and water.

EXAMPLES

In these example implementations, one deposition step is eliminated since standard CMOS metal layers are used to implement the transducers' structures. The maturity and precision of the standard 0.6 µm CMOS technology enables us to manufacture very well-defined metal features to implement the transducers, with minimum widths of 0.9 µm, resulting in very high frequency resonators of 1.02 GHz.

These examples present the design, fabrication, equivalent circuit model and characterization measurements of three two-port resonators. The design of the CMOS SAW resonators is described first, where the key design factors that affect the resonant frequency and quality factor are highlighted. Next, the fabrication sequence of implementing the surface acoustic wave resonators in CMOS with three additional post-processing steps is illustrated in detail. Characterization of the piezoelectric zinc oxide layer using x-ray diffraction, scanning electron microscopy (SEM) and atomic force microscopy is also reported. The fabricated resonators were measured to obtain its $S_{21}$ and $S_{11}$ transmission and reflection characteristics. To verify the resonant frequency of the device, finite element modeling of the device was also done using CoventorWare®. Based on the measurement results and the fabrication layers of the CMOS resonators, an equivalent circuit model specifically for two-port CMOS surface acoustic wave resonators was developed. Simulations using the developed equivalent circuit were compared with the experimental measurements of the fabricated device.

Example

II. Resonator Design

A. Resonator Structure

The structure of a two-port CMOS SAW resonator consists of input and output interdigital transducers, which are flanked by a bank of shorted reflectors on each side. Shorted reflectors have been shown to have less spurious effects compared to unconnected reflectors [5] and have been used in all our designs. When a sinusoidal signal is injected at the input port, acoustic waves propagating in both directions are generated in the piezoelectric zinc oxide layer. The acoustic waves are detected and translated back into an electrical signal at the output port. The reflectors minimize the losses by containing the acoustic waves within the cavity, to create standing waves or resonance.

Figure 10:
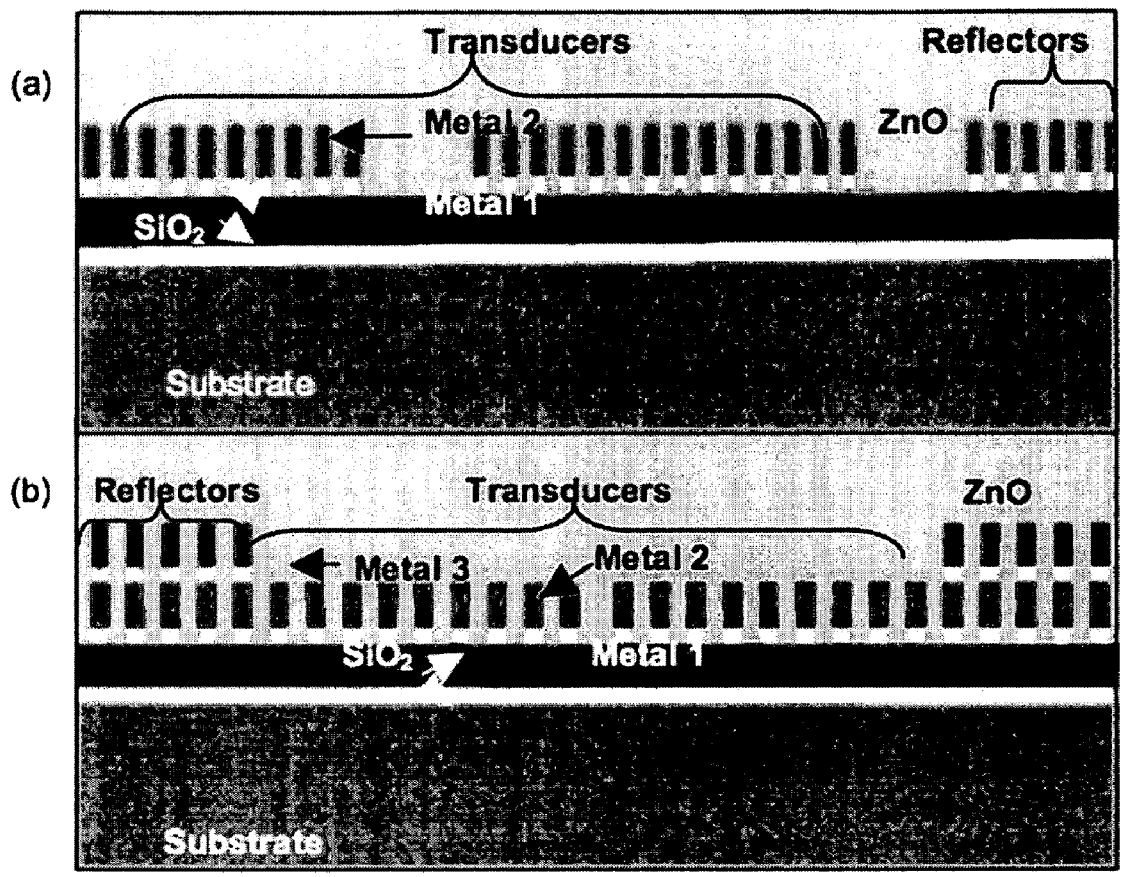
FIG. 10 is a graphic and shows (a) Cross-section of CMOS SAW resonator designs 1 and 2 utilizing two CMOS metal layers. The ground shield was implemented using Metal 1 and both the reflectors and transducers were implemented using Metal 2. (b) Cross-section of CMOS SAW resonator design 3 utilizing three CMOS metal layers. The ground shield was implemented using Metal 1 and both the reflectors and transducers were implemented using Metal 2. Additional acoustic wave containment was provided by an extra layer of reflectors, implemented using metal 3.

FIG. 10 (a) illustrates the cross-section of the CMOS resonator implemented for design 1 and design 2. This implementation utilized two CMOS metal layers, namely metal 1 for the ground shield and metal 2 for the reflectors and transducers. In an effort to improve the quality factor of the device, the third resonator utilized all three available metals in the CMOS 0.6 µm technology. For this implementation, as shown in FIG. 10 (b) both metal 2 and metal 3 were used as reflectors to contain the acoustic waves propagating above the transducer.

B. Resonator Design

The schematic of a two-port resonator, its important design parameters and equations are shown in FIG. 11. For preliminary design, the acoustic wave velocity was assumed to be 3600 m/s [7]. The highest resonant frequency that can be designed for the CMOS 0.6 µm technology used the minimum metal 2 feature size of 0.9 µm for the interdigital finger width (λ/4). The periodic spacing of the interdigital transducers is then calculated as λ=3.6 µm and is shown in Table 1 as Resonator 1. It is assumed that the acoustic wave will penetrate the reflector array for a length of Lp, at which point the wave will be totally reflected [5]. Table 1 illustrates the design parameters of the three implemented resonators. The designs varied λ, to verify the relationship between the fr and λ. The designs also varied the number of reflectors (N).

Table 1
CMOS SAW 2-Port Resonator Design Parameters

TABLE 1

CMOS SAW 2-PORT RESONATOR DESIGN PARAMETERS

| Resonator | λ (µm) | $f_r$ (GHz) | W (µm) | N | Lg (µm) | Lc (µm) |
|---|---|---|---|---|---|---|
| 1 | 3.6 | 1.000 | 144 | 39 | 7.2 | 7.2 |
| 2 | 4.2 | 0.857 | 168 | 100 | 1.05 | 2.1 |
| 3 | 6 | 0.600 | 160 | 33 | 1.5 | 3 |

Example

III. Resonator Post-CMOS Processing

The SAW resonator fabrication can be described using three step post-CMOS fabrication process. In this work, 0.6

μm American Microsystems Incorporated (AMI) CMOS 3-metal, 2-poly process was used. Standard CMOS layers were used to implement the resonator's interdigital transducers, reflectors and the ground shield, which are implemented using metal1 and metal2 CMOS, respectively. The ground shield is crucial for elimination of electromagnetic feedthrough and isolation from substrate noise [7]. For future integration with circuits, all post-processing steps were carefully selected such that no process will require temperatures greater than 400° C. to ensure compatibility with the integrated circuitry. Circuits can be implemented using metal 1 and metal 2 with metal 3 as protection against the adverse effects of the post-processing.

A. Reactive-Ion-Etching

Figure 12:
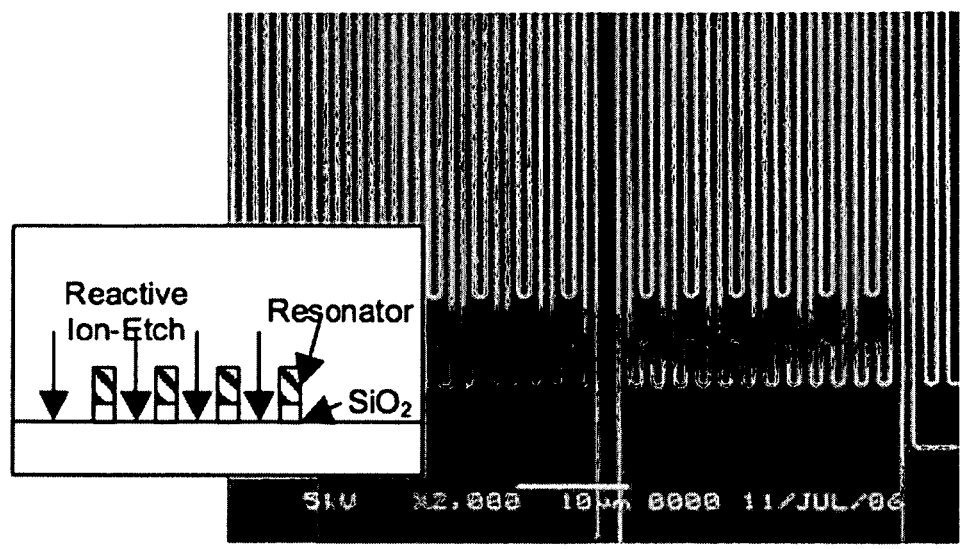
FIG. 12 is a microphotograph and graphic inset and shows Resonator's interdigital transducers and reflectors after reactive-ion-etch. Inset: Cross-section of etched interdigital fingers.

The first post-processing step requires releasing the SAW electrodes from the insulating SiO2 layer. It was reported in [14] that reactive-ion-etching (RIE) can be used to remove oxide between interdigital transducer fingers. Timed RIE process was used to etch the 2.5 μm thick oxide layer. The calculated etch rate was 0.2174 μm/min, which was sufficient to remove all the oxide surrounding the metal electrodes. Contact test was performed to ensure complete release of the metal electrodes. FIG. 12 shows the complete removal of SiO2 from the interdigital fingers and reflectors.

B. Zinc Oxide Deposition and Characterization

Zinc oxide has been chosen as the piezoelectric material due to is superior acoustic propagation and transduction compared to other integrated-circuit compatible piezoelectric layers such as AlN [7]. To obtain maximum piezoelectric coupling, $2.0 < khZnO < 4.2$ where $k=2\pi/\lambda$ [7]. For our designs of 3.6 μm$<\lambda<$6 μm, the optimum thickness of zinc oxide was calculated to be 2.4 μm.

Zinc oxide deposition was performed using radio frequency (RF) magnetron sputtering, where the 2.4 μm thick ZnO layer was deposited at a rate of 0.297 μm/hr over the entire die area. Sputtered ZnO films are preferred since these layers are highly oriented and dense [15]. The temperature of the sample was kept below 400° C. to ensure compatibility with the integrated circuitry. The sputtering was conducted with 50/50 gas flow mixture of Ar/O2 with power of 150 W.

Figure 13:
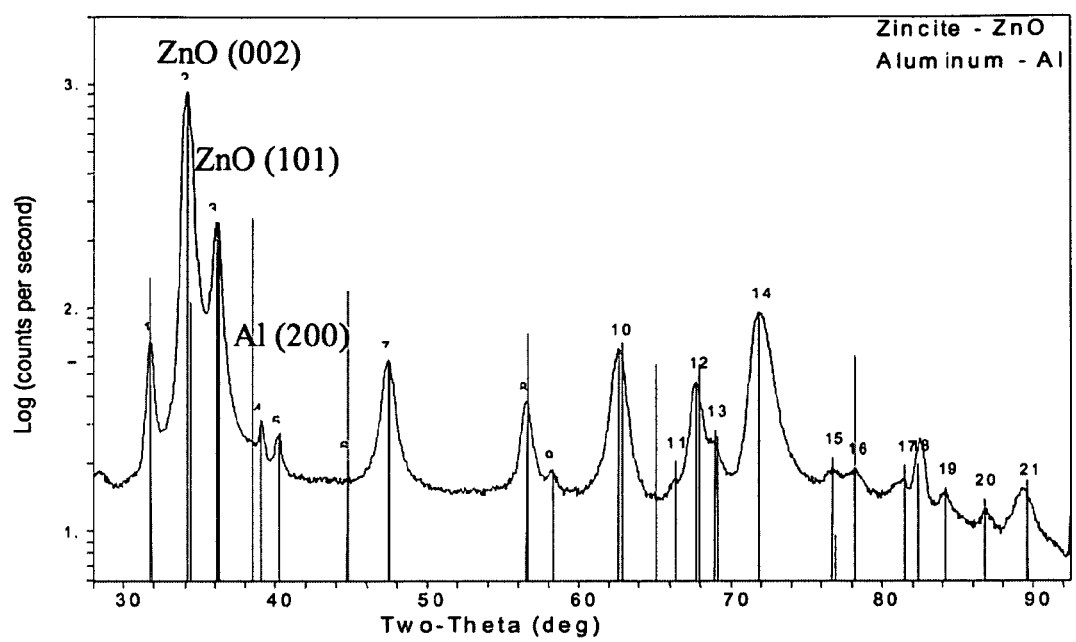
FIG. 13 is a graph and shows X-Ray Diffraction 2θι-scan of CMOS resonator chip. Height of ZnO (002) is 2.9 cps.

To evaluate the quality of the ZnO, the X-ray diffraction 2θι-scan was performed on the deposited ZnO on CMOS SAW resonator samples to determine the ZnO's crystal orientation. Highly oriented ZnO films produce high reflection intensity from the (002) planes and have been reported to have good piezoelectric coupling coefficient κ [15]. FIG. 13 illustrates the results of the X-ray diffraction test performed on the 0.6 μm CMOS SAW resonator sample. The reflection intensity of each phase is measured in log scale of counts per second. It indicates that the ZnO crystals are oriented at the (002), since the highest peak occurs at 34.20 with 2.9 counts per second (cps). The Al layer has its peak at (200) where θ=44.720. The surface morphology of the zinc oxide layer was also investigated using atomic force microscopy, where the root mean-square roughness of the layer was measured to be 0.05 μm.

C. Zinc Oxide Etching

Figure 14:
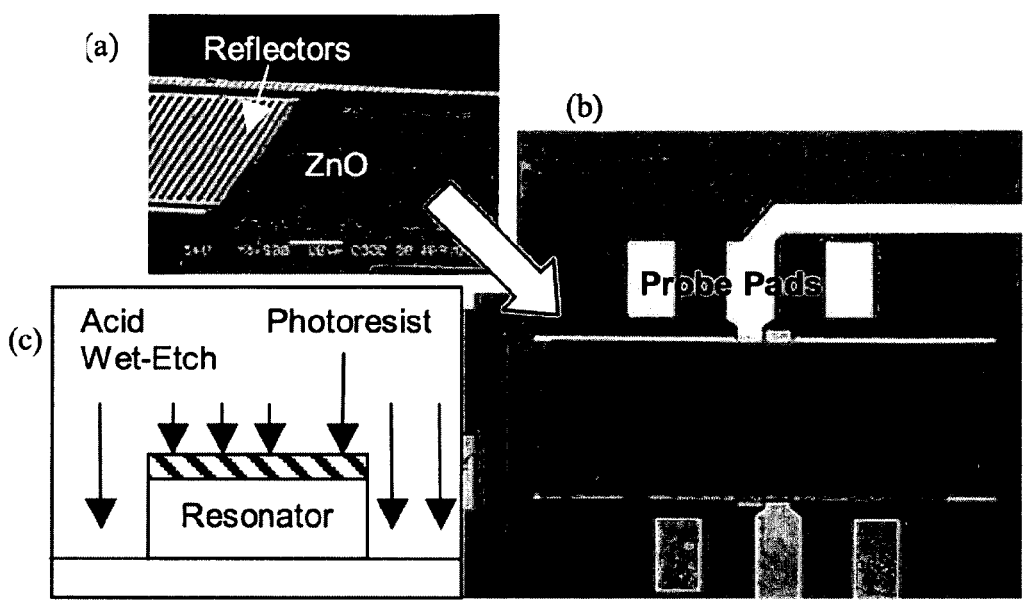
FIG. 14 is a SEM and microscope image along with a graphic and shows SEM and microscope image of CMOS SAW resonator 2. (a) Etched edge of ZnO. (b) Resonator 2 after ZnO etching. (c) Acid wet-etch process where resonator is masked using photoresist.

The ZnO covered die was wet-etched to enable access to the resonator's pads for probing [10]. The resonator area is masked using standard lithography process using 1.8 μm thick liquid photoresist. The small size (1.5 mm×1.5 mm) of the samples creates a tendency of photoresist buildup at its edges. To solve this, the small die is first glued at the far edge of a large circular wafer before photoresist spinning. The die and wafer are spun at 4000 rpm. This method produces uniform photoresist throughout the sample. The sample is then patterned by placing the sample in a mask aligner and exposed to ultraviolet light for 18 s. The mask is a set of three squares, which only covers the resonators. The sample is placed in developer solution for 60 s to develop the pattern. Once the protective photoresist has covered the resonator, the sample is immersed in an etching solution, which is selective to the photoresist as shown in FIG. 14. (c). To etch the zinc oxide, an etching solution that does not adversely affect the piezoelectric properties of ZnO is required. The H3PO4: C6H8O7:H2O solution have been reported to produce very steep etch slopes in [16]. This etching solution with concentrations 1:1:80 was used to etch the sample for 158 s. The calculated etch rate was 1.4 μm min. The SEM image of the etched ZnO shown in FIGS. 14 (a) and (b) illustrates very well defined etched edges of the piezoelectric ZnO layer.

Example

IV. Resonator Modeling and Simulation

A. Equivalent Circuit Model

Based on the fabrication layers of the device and the equations derived by Morgan [11], Zeijl [12] and Datta [5], the equivalent circuit model tailored specifically for standard CMOS two-port resonator was developed. The equivalent circuit for the resonator can be divided into two distinct parts, namely the acoustic and the parasitic components.

The acoustic component describes the propagation of the acoustic wave within the cavity. The acoustic waves, generated by the interdigital fingers propagate in the piezoelectric layer and act as a resonator and consist of Cx, Rx, Lx and Cf.

Figure 15:
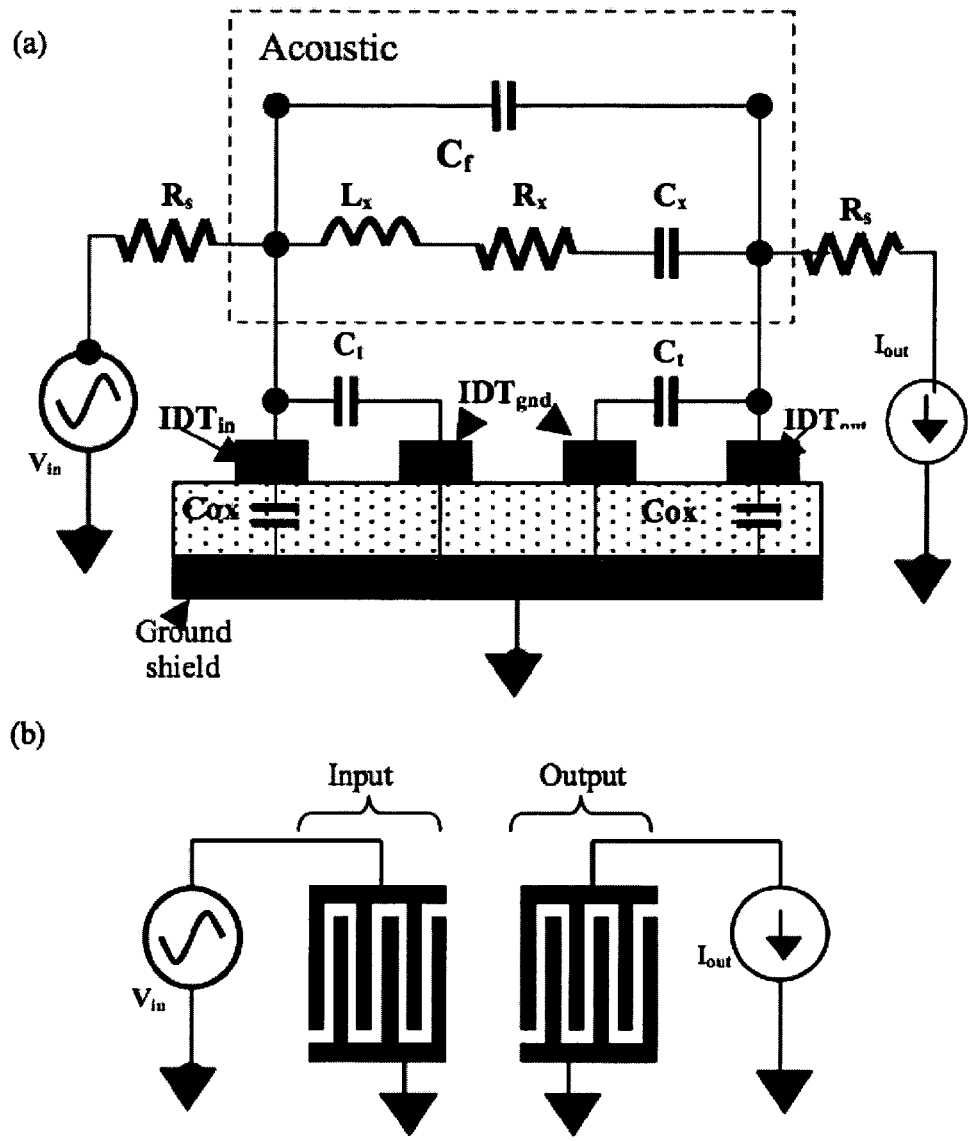
FIG. 15 is a graphic showing a cross section and a top view of a resonator.

The parasitic component consisting of Rs, Cox and Ct exist due to the structure and the layers of the resonator. As shown in FIG. 15 (a), the interdigital fingers were constructed using metal 2 layer on top of SiO2. Underneath the oxide is the ground metal 1 shield. This structure creates two parasitic capacitances namely Ct and Cox. The electrostatic capacitance (Ct) is the capacitance of the parallel plates of the interdigital transducers and is described in (2). Ct is proportional to the width of the aperture (W) and the number of transducer pairs (Nt). Since the capacitive parallel plates of the interdigital transducers are placed within the piezoelectric material, the relevant permittivity constant (∈) is the effective dielectric permittivity of zinc oxide, ∈=135 pF/m [12].

$$C_t = W \in N_t \quad (1)$$

Cox is the oxide capacitance between the input and output port and the ground shield and is calculated using (2). Cox is not present between IDTgnd and the ground plane since in our design, there exists a via or connection between IDTgnd and the ground plane. It is assumed that the resistance at the input (Rf) is the impedance of the network analyzer or 50 Ohms.

$$C_{ox} = W \in_{ox} N_t \quad (2)$$

As shown in FIG. 15 (b) when a sinusoidal signal Vin is applied to the input port, propagating acoustic waves will be generated in the piezoelectric layer above the interdigital fingers. The incident acoustic waves will induce current Iout in the output port. The ratio Iout/Vin is known as the admittance (Yt). The real part of the admittance is known as radiation conductance, which represents electrical-to-acoustic energy conversion. The radiation conductance (Ga) at resonant frequency (fr) is approximated as in (3).

$$G_a = 8\kappa^2 f_r C_t N_t^2 \quad (3)$$

The piezoelectric coupling coefficient (κ) was obtained from [7] where the phase velocity (v) and κ have been calculated and graphed for the multi-layer ZnO—SiO2-Si structure with varying ZnO thicknesses. κ2 has values ranging from 0 to 0.032. For this design, κ2=0.017. The interdigital fingers are placed within a cavity formed by the reflectors. The reflectors contain the acoustic waves within the cavity, reducing the losses of the acoustic waves propagating outwards. To describe the effect of these reflectors, the reflectivity (r) a single strip was calculated. The expression used to describe the reflectivity in an array of short-circuited reflectors was provided by Datta in [13] and is shown in (4). The variables used in (4) were defined as follows where Δ=ηπ and the Legendre polynomials were calculated as P0.5(cos Δ)=1.5061 and P−0.5(cos Δ)=1.3280. For this design, the metallization ratio, η was set to 0.5. The array reflectivity is described using (5) and is a function of both r and the number of reflectors (N).

$$r = j\left|\frac{1}{2}\kappa^2\right|\frac{\pi}{2}\left((-\cos\Delta) + \frac{P_{0.5}(\cos\Delta)}{P_{-0.5}(-\cos\Delta)}\right) \quad (4)$$

$$|\Gamma| \equiv \tanh N|r| \quad (5)$$

All the equations above were coded into MATLAB® to determine the device's array reflectivity (Γ). For resonator design 1, r was found to be 0.01511 and Γ=0.8278 where λ=3.6 μm, N=39 and κ2=0.017. Since Γ<1, the acoustic wave will penetrate the reflector array till a point Lp, where it is assumed that the wave is totally reflected [5]. The effective penetration length, Lp was calculated using (6). For resonator 1, Lp=59.436 μm.

$$L_p = \frac{\lambda}{4|r|} \quad (6)$$

The acoustic wave variables Cx, Rx and Lx are based on the transmission line model provided by Zeijl [12] and Datta [13]. Near fr, the device acts as a resonator, which can be modeled as an LC tank circuit. Rx is the inverse of the radiation conductance of the interdigital transducers (Ga). Due to the effect of the reflectors, Ga is increased by a factor related to the array reflectivity (Γ) and δ which is half of the effective cavity length as shown in (7) and (8).

$$G_s(f_r) = G_a \frac{1 + 2\Gamma\cos(4\pi\delta/\lambda) + \Gamma^2}{1 - \Gamma^2} \quad (7)$$

$$\delta = L_g + L_p + \frac{N_r \lambda}{2} \quad (8)$$

The acoustic resistance Rx is inversely proportional to Gs and was described in (9). The inductance (Lx) described in (10) is related to the total effective cavity length (L+2Lp), Γ, Ga, δ and the acoustic velocity (v). Since the device is a resonator, the acoustic capacitance (Cx) is a function of Lx as described in (11). Due to the proximity of the input and output port, a feedthrough capacitance (Cf) exists and determines the parallel resonance frequency (fp). Cf can be calculated using (12) where t is the thickness of metal 2 and was defined as 1.6 μm [17]. The quality factor of the resonator is a function of the total effective cavity length (L+2Lp) and array reflectivity (Γ) as shown in (13). A summary of the equivalent circuit model values is shown in Table 2. In comparison with Table 1, the resonators were designed to maximize Γ without occupying too much area. Based on (4), array reflectivity (Γ) close to 1 can be achieved by having a many reflectors, at the expense of consuming large area. Resonator 2 with N=100, has the maximum Γ and correspondingly the highest Q.

TABLE 2

CMOS SAW 2-PORT RESONATOR DESIGN RLC

| Resonator | λ (μm) | $R_x$ (kΩ) | $C_x$ (aF) | $L_x$ (μH) | $C_f$ (fF) | $C_{ox} + C_t$ (pF) | Γ | $Q_s$ | $f_s$ (MHz) | $f_p$ (MHz) |
|---|---|---|---|---|---|---|---|---|---|---|
| 1 | 3.6 | 2.16 | 332 | 71.6 | 5.6 | 0.238 | 0.83 | 684 | 1042.9 | 1032.2 |
| 2 | 4.2 | 13.0 | 48.5 | 603 | 22.4 | 0.278 | 0.99 | 29059 | 930.92 | 930.95 |
| 3 | 6 | 7.56 | 208 | 335 | 14.9 | 0.265 | 0.87 | 683 | 602.40 | 603.76 |

$$R_x = \frac{1}{G_s(f_r)} \quad (9)$$

$$L_x = \frac{L + 2L_p}{G_a v} \cdot \frac{\Gamma^2}{1 + 2\Gamma\cos(4\pi\delta/\lambda) + \Gamma^2} \quad (10)$$

$$C_x = \frac{1}{4\pi^2 f_r^2 L_x} \quad (11)$$

$$C_f = \frac{\varepsilon W t}{L_c} \quad (12)$$

$$Q = \frac{2\pi}{\lambda}(L + 2L_p)\frac{\Gamma^2}{1 - \Gamma^2} \quad (13)$$

B. Finite Element Simulation

The resonant frequency of the device was verified using CoventorWare®'s three-dimensional finite element method analysis. The device was modeled as an electromechanical system where the solver was used to compute mechanical displacement in the piezoelectric layer due to an electrical excitation. The resonant frequency of the device occurs when there is maximum displacement of the piezoelectric layer in all directions. To model the composite resonator structure, a seven-step fabrication process describing CMOS and its MEMS post-processing was utilized and are shown in Table 3.

TABLE 3

CMOS SURFACE ACOUSTIC WAVE RESONATOR FABRICATION LAYERS

|   | Step Name | Layer Name | Material Name | Thickness (μm) |
|---|---|---|---|---|
| 0 | Substrate | Substrate | SILICON | 50 |
| 1 | Stack Material | SiO$_2$ | OXIDE | 0.6 |
| 2 | Conformal Shell | CMF | Al (Film) | 1.5 |
| 3 | Stack Material | SiO$_2$ | OXIDE | 0.6 |
| 4 | Conformal Shell | CMF | Al (Film) | 1.6 |
| 5 | Straight Cut | | | |
| 6 | Planar Fill | ZnO | ZnO | 2.4 |

Layers 0-4 describes the resonator's layers implemented using CMOS, while layer 5 and layer 6 describe the reactive-ion-etching and RF sputtering of the ZnO layer respectively. The piezoelectric strain matrix coefficients used for the ZnO were $d31=-5.43\times10-6$, $d32=-5.43\times10-6$, $d33=1.167\times10-5$, $d24=-1.134\times10-5$ and $d15=-1.134\times10-6$ [18].

Figure 16:
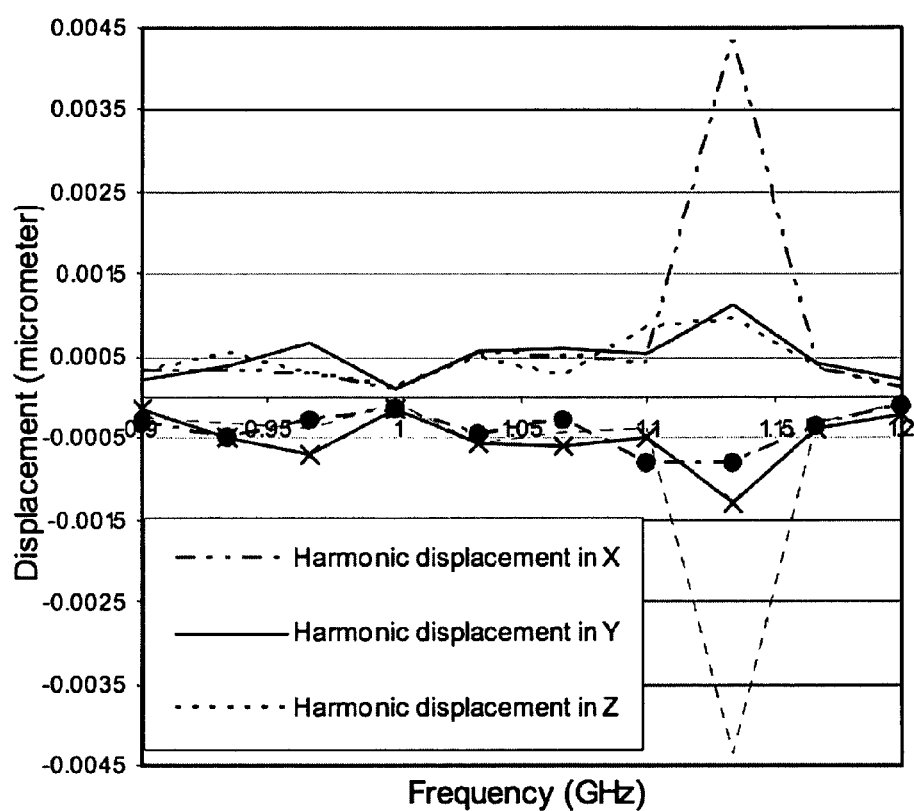
FIG. 16 is a line graph and shows harmonic analysis of CMOS SAW resonator design 1.

The device's resonant frequency can be determined using harmonic analysis in CoventorWare®. Harmonic analysis provides the structure's response to a continuous harmonic excitation. For resonator 1, harmonic excitation was applied as a sinusoidal waveform of 3 V amplitude with frequencies between 1 GHz to 1.3 GHz at the resonator's interdigital transducers. Due to the piezoelectric properties of the zinc oxide layer, the induced electrical excitation will produce mechanical displacement, which in turn generates the surface acoustic wave in the ZnO layer. As shown in FIG. 16, the maximum displacement in all directions occurs at 1.13 GHz for resonator 1 with $\lambda=3.6$ μm and can be compared to its design series resonant frequency of 1.0320 GHz as shown in Table 2. The propagating acoustic wave in the piezoelectric layer has maximum displacement of 0.004 μm.

Example

V. Experimental Measurements and Discussion

Figure 17:
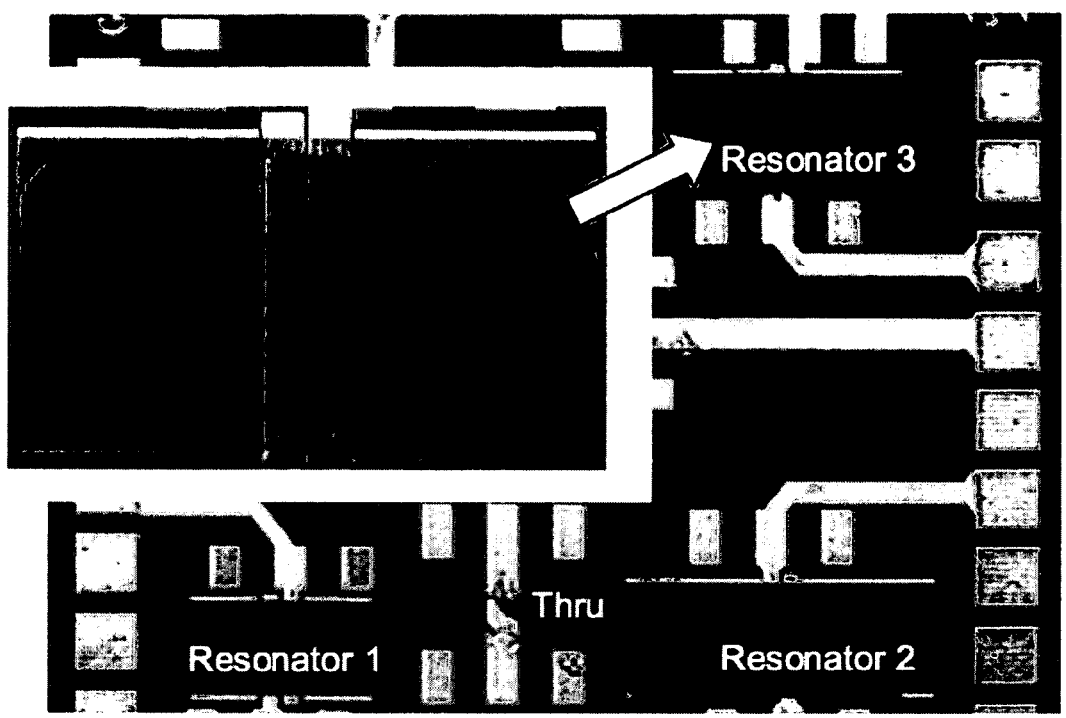
FIG. 17 is a microscope image and shows a whole chip consisting of three resonators.
Figure 18:
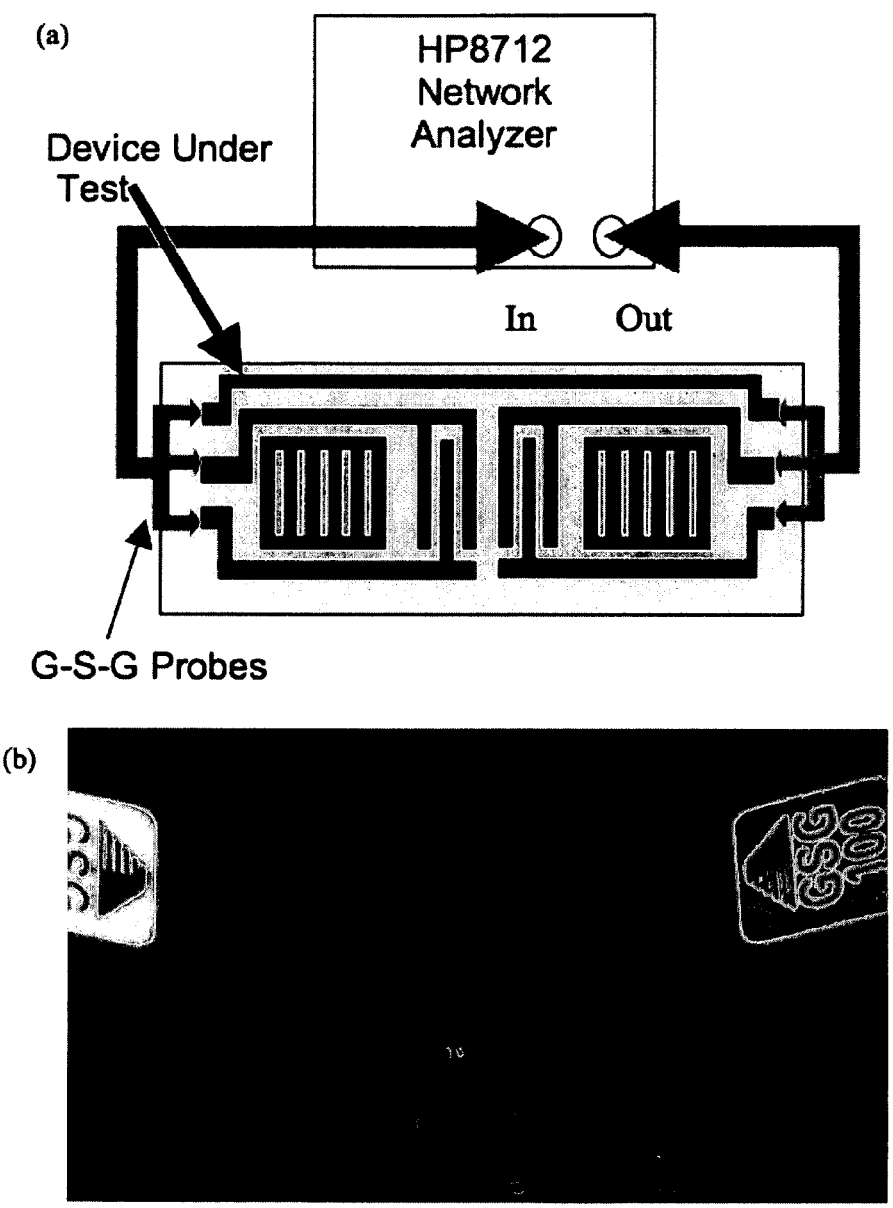
FIG. 18 is a graphic (a) and (b) a photo showing the experimental setup of the device with probes connected.

The designed chip consisting of three resonators is shown in FIG. 17. To obtain S21 and S11 measurements, each resonator was probed using two coplanar G-S-G probes in the Cascade Microtech 9500 Parametric Probe Station connected to the HP8712 network analyzer. The coplanar probes were connected to the network analyzer using cables, SMA and N connectors. The experimental setup is shown in FIG. 18.

A Thru calibration structure was also included in the design to improve measurement accuracy. Both metal 2 and metal 1 in CMOS was used to implement the Thru structure. To avoid the probes crashing and damaging one another, the distance between the two probes was set to be 200 μm [19].

A. Analysis of Measurement Results

Figure 19:
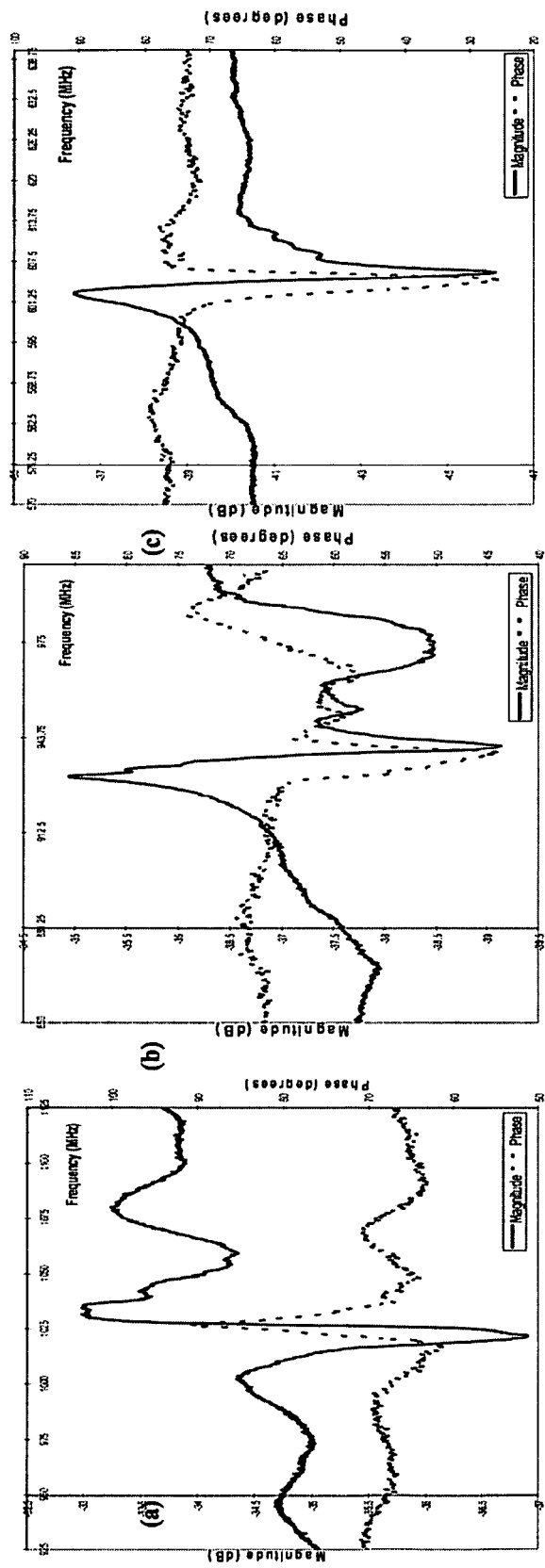
FIG. 19 is a set of three line graphs and shows magnitude and phase s21 measurement results of three resonators.
Figure 20:
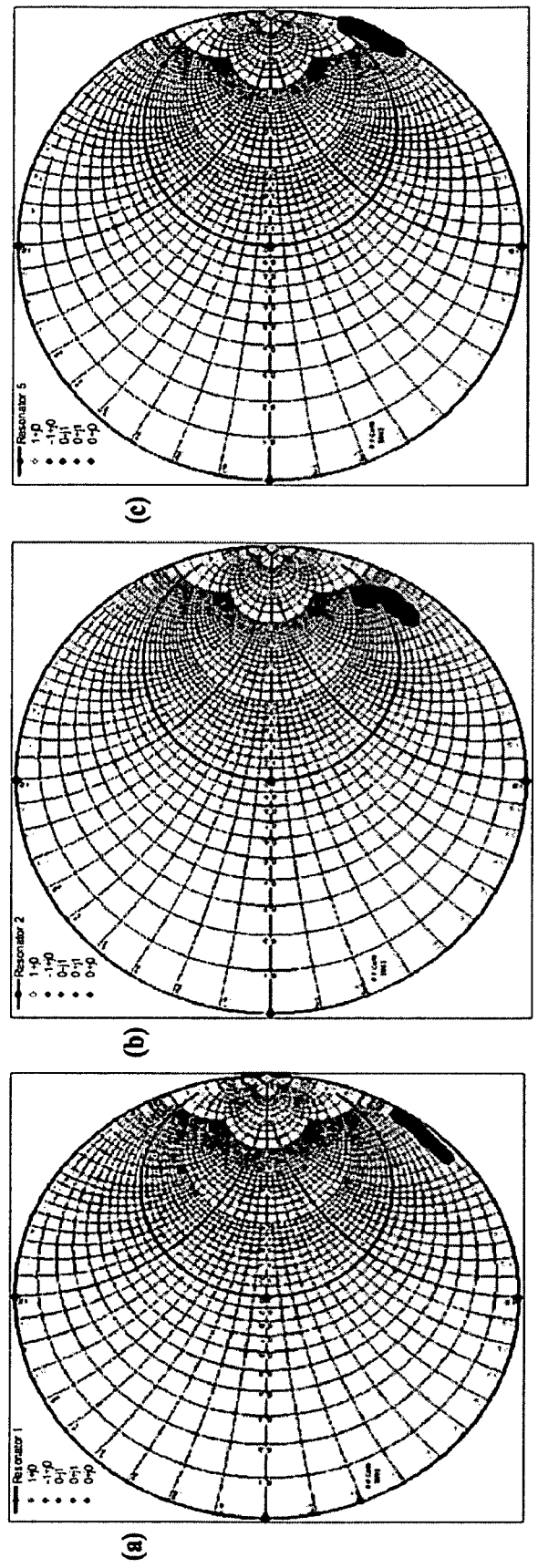
FIG. 20 is a set of three graphs and shows S11 measurement results of three resonators.

The S21 measurements provide the insertion loss (IL), series resonant frequency (fs) and parallel resonant frequency (fp). The S21 transmission magnitude and phase measurements as well as the S11 reflection measurements of resonators 1, 2 and 3 are shown in FIG. 19 and FIG. 20 respectively. Resonator 3 shown in FIG. 19 (c) exhibited the best transmission characteristics, having the highest parallel quality factor of 284.98. The high quality factor of this resonator is due to its structure, where an additional layer metal 3 of reflector was implemented as shown in FIG. 18 (b). Based on Morgan [11], the maximum energy of the propagating acoustic wave is within λ thickness of the piezoelectric layer. For our design, the thickness of ZnO was 2.4 μm and it is assumed that the energy of the acoustic wave is contained within the entire thickness of the piezoelectric layer. The first layer of reflector structure constructed using metal 1 has a total height of 1.9 μm which is insufficient to reflect all the propagating acoustic waves. Stacking an additional metal 3 layer of 1.6 μm with additional 0.3 μm layer of SiO2 will result in a total height of 3.8 μm of for the reflector structure. This height is greater than the thickness of the sputtered ZnO layer and is sufficient to reflect all the energy of the propagating acoustic wave. This results in suppression of harmonics, having a single parallel and series resonant frequency as shown in FIG. 19 (c).

Resonator 1 shown in FIG. 19 (a) exhibits transmission characteristics which are not well-defined, having very low Qs and Qp of 33.32 and 44.43 respectively. The low Q can be attributed to both the insufficient height of the reflectors as well as the design. With reference to Table 1 where both Lg and Lc of Resonator 1 was set to 7.2 μm or 2λ. This results in a distorted wave since $L/\lambda=17$ is not an odd multiple of $\lambda/2$. Much improved resonant characteristics are seen in both Resonator 2 and Resonator 3 where $L/\lambda=10.5$ for both resonators as shown in FIGS. 19 (b) and (c) respectively.

B. Measurement of Surface Acoustic Wave Velocity

In comparison to Table 1, the resonators were designed to have series resonant frequencies of 1 GHz, 857 MHz and 600 MHz respectively. The measured resonators had series resonant frequencies of 1.032 GHz, 930 MHz and 602 MHz respectively. The difference between the design and measured resonant frequencies can be attributed to the deviation of the acoustic wave velocity value from the assumed 3600 m/s. The acoustic wave velocity of the device can be extracted from the measured fs based on $v=fs\lambda$. Table 4 shows the variation of surface acoustic wave velocity at different λ. The acoustic wave velocity is a function of khZnO where $k=2\pi/\lambda$ and hZnO is the thickness of the ZnO layer. For this chip hZnO=2.4 μm. It has been shown in [7] that both the acoustic wave velocity and the piezoelectric coupling coefficient (κ) is a function of khZnO, where the optimum is between 2 and 4.2. It can be seen from the Table 4 that at khZnO=3.5904, the extracted acoustic wave velocity is at its highest, indicating the maximum piezoelectric coefficient. This indicates that to obtain maximum coupling, each design with different λ should have different thickness of zinc oxide. This however, is impractical for this chip since all the resonators with different λ were placed on the same chip and had to have a constant hZnO for all three designs. This resulted in different κ and different acoustic wave velocity for each resonator.

TABLE 4

EXTRACTED SURFACE ACOUSTIC WAVE VELOCITY AT DIFFERENT λ

| λ | $(2\pi/\lambda) \cdot h_{ZnO}$ | Measured $f_s$ | Extracted SAW velocity |
|---|---|---|---|
| 3.6 μm | 4.1888 | 1.03275 GHz | 3717.9 m/s |
| 4.2 μm | 3.5904 | 0.93094 GHz | 3909.9 m/s |
| 6 μm | 2.5133 | 0.60256 GHz | 3615.4 m/s |

C. Extraction of Equivalent Circuit Parameters from S21 Measurements

The S21 measurements can also be used to extract the equivalent RLC circuit parameters of the resonators [20], [21]. The S21 measurements can be used to calculate the series quality factor (Qs) and parallel quality factor (Qp) based on the 3 dB bandwidth at the series and parallel resonant frequencies respectively, $Q=f/\Delta f3$ dB. Based on the equivalent circuit model shown in FIG. 15, the equations of the impedances for the equivalent circuit can be expressed. The average value of $Q=0.5(Qs+Qp)$ and the calculated value of Rx as shown in Table 2 was used to obtain Lx as described in (14). Since the device operates as a resonator, Cx can be calculated using (15) based on Lx and fs.

TABLE 5

CMOS SURFACE ACOUSTIC WAVE MEASURED PERFORMANCE
AND EXTRACTED EQUIVALENT CIRCUIT PARAMETERS

| | Measured | | | | Extracted | | | | |
|---|---|---|---|---|---|---|---|---|---|
| Design | $f_s$ (GHz) | $f_p$ (GHz) | $Q_s$ | $Q_p$ | $R_x$ (k$\Omega$) | $L_x$ ($\mu$H) | $C_x$ (aF) | $C_f$ (fF) | $C_{ox} + C_f$ (fF) |
| 1 | 1.03275 | 1.02200 | 33.31 | 44.43 | 10 | 464.91 | 51.66 | 28.0 | 238.27 |
| 2 | 0.93094 | 0.94094 | 46.52 | 86.03 | 15 | 306.39 | 94.57 | 23.5 | 278.00 |
| 3 | 0.60256 | 0.60588 | 60.56 | 284.98 | 10 | 791.82 | 87.98 | 23.5 | 264.75 |

The circuit can be divided into two sets of parallel branches. The impedance of the acoustic branch (Zac) consisting of the extracted values of Rxe, Cxe, Lxe and Cfe is expressed in (16). The parasitic parallel branch containing Rs and (Ct+Cox) calculated from Section IV.A is described as (Zp) in (17). The insertion loss of the circuit is a function of these two impedances Zp and Zac and is shown in (18).

$$Z_{ac} = \frac{R_{xe} + \frac{1}{sC_{xe}} + sL_{xe}}{sC_{fe}\left(R_{xe} + \frac{1}{sC_{xe}} + sL_{xe}\right) + 1} \quad (16)$$

$$Z_p = \frac{R_s}{s(C_t + C_{ox})R_s + 1} \quad (17)$$

$$IL = -20\log\left(\frac{2Z_p}{Z_{ac} + 2Z_p}\right) \quad (18)$$

Figure 21:
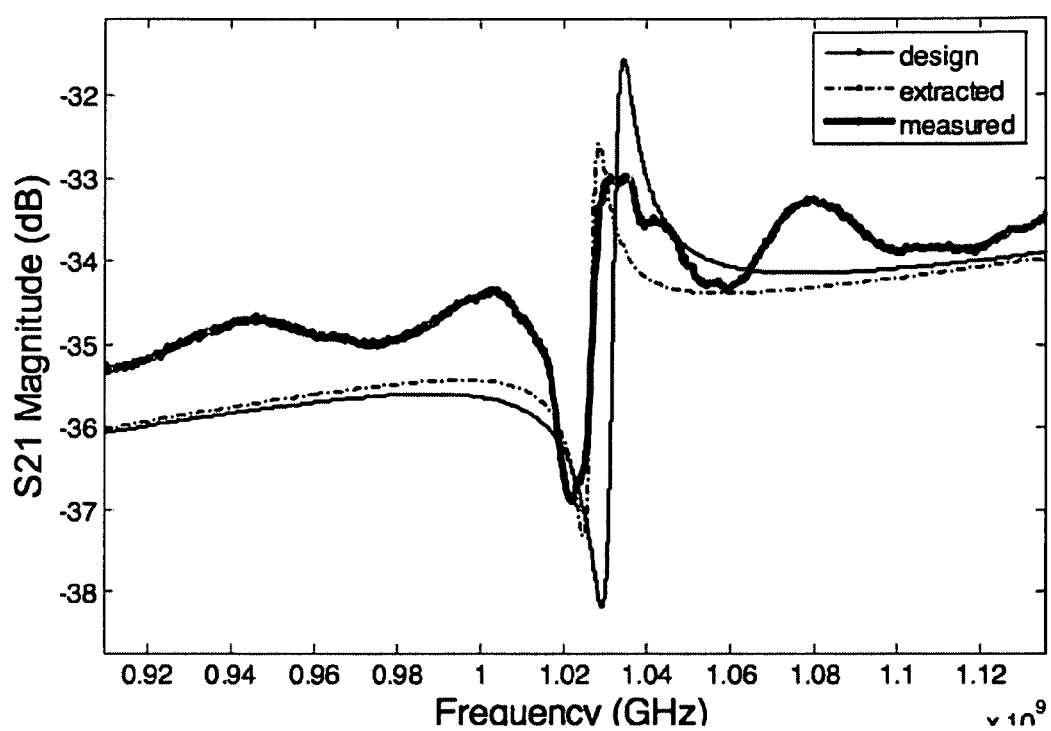
FIG. 21 is a line graph and shows S21 magnitude transmission characteristics of Resonator 1.
Figure 22:
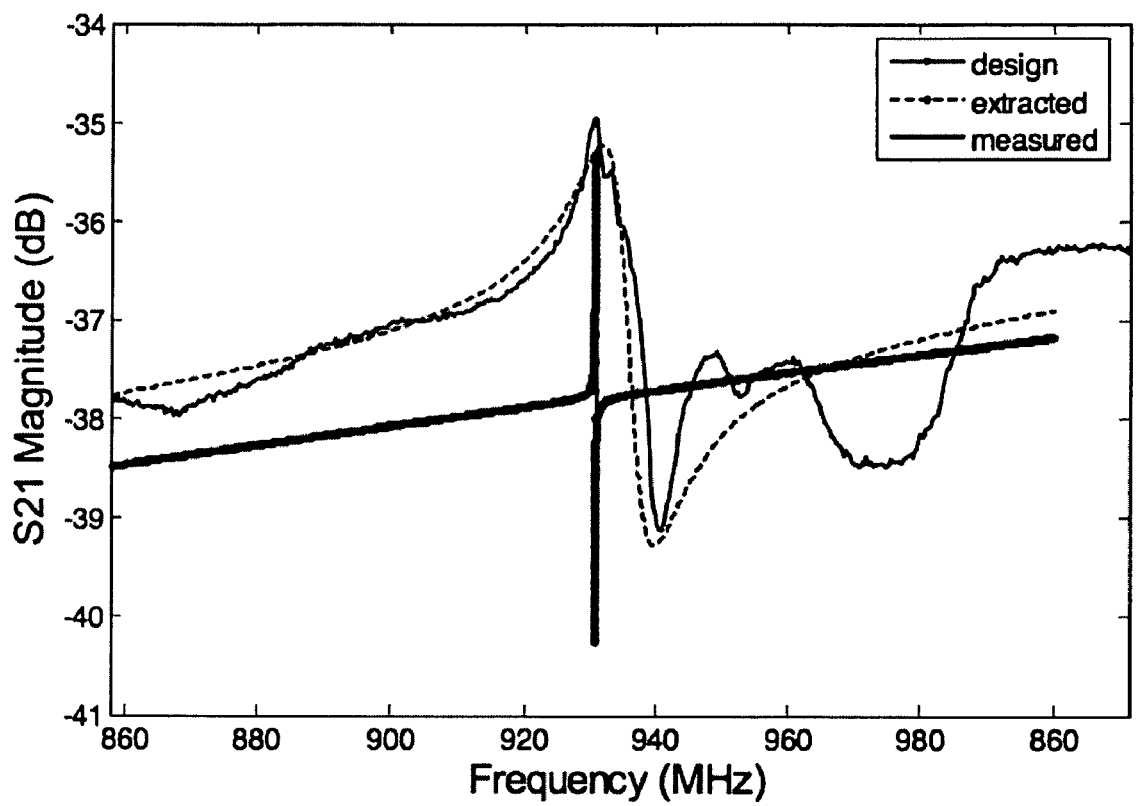
FIG. 22 is a line graph and shows S21 magnitude transmission characteristics of Resonator 2.
Figure 23:
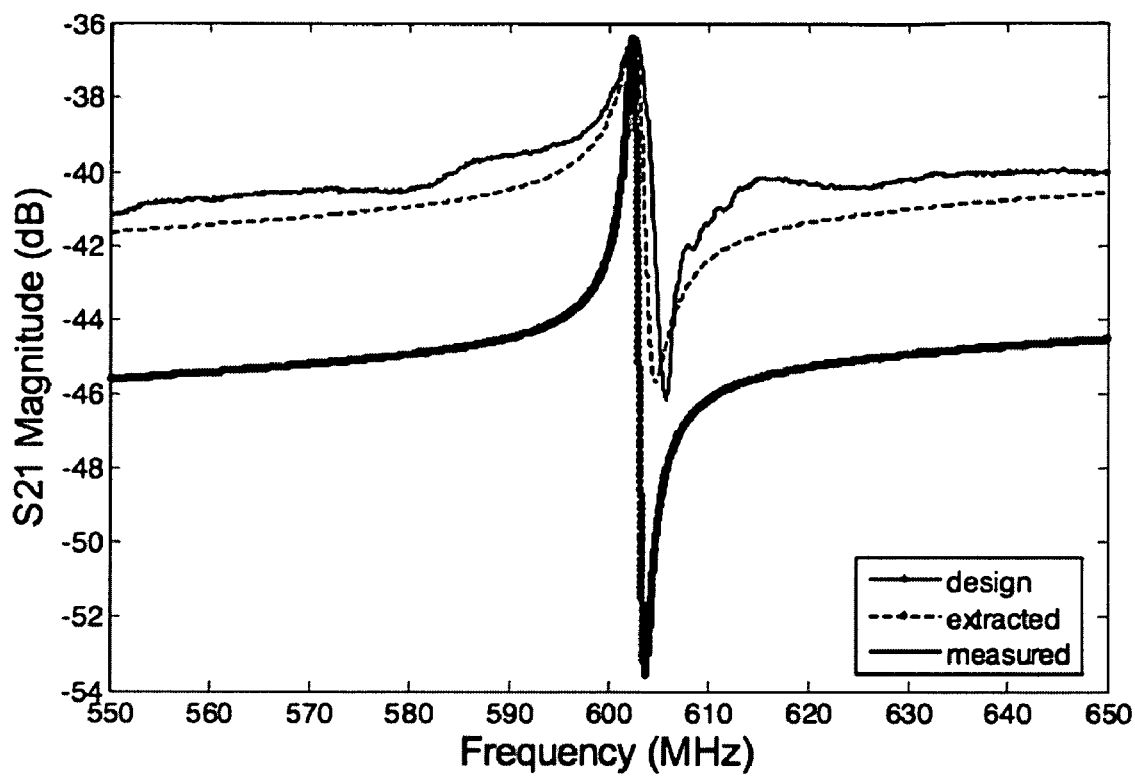
FIG. 23 is a line graph and shows S21 magnitude transmission characteristics of Resonator 3.

The extracted equivalent circuit values are summarized in Table 5. Calculated values of (Ct+Cox) shown in Table 2 were used as a starting point to obtain Lx, Cx, Rx and Cf. The insertion loss of the extracted equivalent circuit was graphed using MATLAB and compared with both the design equivalent circuit developed in Section IV. A and the measurement results. These graphs were prepared for each resonator and are shown in FIG. 21, FIG. 22 and FIG. 23 respectively. Table 6 shows comparison of design, extracted and measured quality factors for all three resonators.

TABLE 6

COMPARISON OF MEASURED AND
EXTRACTED QUALITY FACTORS

| | Measured | | Extracted | | | Design |
|---|---|---|---|---|---|---|
| | $Q_S$ | $Q_P$ | $Q_S$ | $Q_P$ | $C_f$ (fF) | $C_f$ (fF) |
| 1 | 33.31 | 44.43 | 26.98 | 74.97 | 28.0 | 5.6 |
| 2 | 46.52 | 86.03 | 65.70 | 106.65 | 23.5 | 22.4 |
| 3 | 60.56 | 284.98 | 94.75 | 186.00 | 23.5 | 14.9 |

FIG. 21 shows the simulated and measured S21 magnitude transmission characteristics of Resonator 1. From the graph, it can be seen that the design curve shows much lower insertion loss of −31 dB compared to the measured results of −33 dB. The extracted curve shows closer results to the measured curve, having insertion loss of −32.6 dB. The deviation between the measured and design curves can be attributed to the difference between the design Rx=2.16 kOhms and the extracted Rx=10 kOhms. For the design, Rx was calculated based on both the conductance of the device (Gs) and the array reflectivity (Γ). Gs as shown in (1) is highly dependent on the piezoelectric coupling coefficient (κ). Initial values of κ=0.017 had been taken from [7] and can serve only as an estimation of the actual value since piezoelectric coupling coefficients are sensitive to variations in processing. It has been shown in [7] and [8] that κ is dependent on khZnO showing maximum κ=0.03 when khZnO=3. As shown in Table 4, khZnO=4.19 for this design where K can be as low as 0.014, depending on the quality of the sputtered ZnO. Additional losses, and further reduction of Gs is also due to the insufficient reflector height, described earlier in Section V.A. The low quality factor can also be attributed to the small number of reflectors N=39 of this resonator, implemented to minimize the total area of the resonator. FIG. 22 shows much better agreement between the design and measurement results. The measured insertion loss was −35 dB whereas the extracted insertion loss was −36 dB. The extracted Rx=15 kOhms was close to the design Rx=13.01 kOhms. The feedthrough capacitance values of both the extracted and design showed a close match to each other, where for the extracted circuit Cf=23 fF and the design Cf=22.4 fF as shown in Table 6. Similar to Resonator 1, the design Q=29059 for Resonator 2 was much higher than the measured Q of 86.03. The low Q of this resonator was attributed to the low coupling coefficient and insufficient height of the reflector which caused additional losses of the acoustic wave and thus reducing the conductance of the device. The extracted quality factors showed a closer match to the measured quality factor after the extracted Rx was increased to include the additional losses. For this design, L/λ=10.5 and the number of reflectors used was 100, resulting in Γ close to 1, which resulted in a well defined series and parallel resonant frequency.

Resonator 3 illustrated in FIG. 23 shows the best results where the measured insertion loss=−36.406 dB, the extracted insertion loss=37.3618 and the design insertion loss=−36.4395. The extracted Rx=10 kOhms was close to the design Rx=7.56 kOhms. The measured quality factor of Qp=285 is the highest compared to the other designs. This high quality factor is due to the increase in height for the reflector structure, greatly reducing the losses of the propagating acoustic waves. This measurement result indicates that a high quality factor can be achieved even with minimum number of reflectors, where N=33 for this design. It also serves to prove that the quality factor and the array reflectivity are highly dependent on the height of the resonator structure rather than the number of reflectors used. This is in comparison with Resonator 2 which had a lower reflector height but a large number of reflectors and produced a low Q.

This work provides both the implementation of an integrated CMOS surface acoustic wave resonator and the development of its equivalent circuit model to support it. This is significant since it demonstrates that the frequency of surface acoustic waves can controlled using interdigital fingers implemented using inexpensive standard CMOS technology with minimum number of additional post-CMOS micromachining processes. Previous implementations [7], [8] or [9] did not utilize standard CMOS process to implement the resonator's interdigital fingers but implemented the fingers using separate deposition steps, resulting in a very high fabrication cost due to the necessity of having very thin and precise interdigital fingers to achieve very high resonant frequencies. The maturity of standard integrated circuit processing technology such as CMOS is very reliable in manufacturing very precise thin metal lines, and for this 0.6 µm CMOS technology used, the minimum metal widths were 0.9 µm, generating a resonant frequency of 1 GHz. Higher frequency resonators can be achieved when smaller CMOS technology feature sizes are used. Currently, the minimum possible CMOS metal feature size is 135 nm and can theoretically create CMOS SAW resonators operating at 7 GHz. Three different resonator designs, operating at different frequencies, 1.02 GHz, 941 MHz and 605 MHz were presented to illustrate the feasibility and the performance of these devices. The measurement results indicate minimum insertion losses in the range −33 dB to −36 dB. The measured quality factor ranged from 33 to 285. Based on the measurement results and the fabrication layers of the device, an equivalent circuit model, tailored specifically to describe the two-port CMOS SAW resonator was developed.

Comparison of the design, extracted and measurement S21 transmission characteristics were presented. It can be seen from these graphs that when losses of the propagating acoustic wave is reduced by increasing the reflector height, the design, extracted and measured results are in accordance with each other. Although the resonators exhibited much lower quality factors than commercial discrete devices which have Qs in the order of 10 000, the quality factors of these devices are much higher than the Qs of integrated LC CMOS resonators which are typically less than 50. LC CMOS resonators are typically used when integrated resonators are required for circuits. The measurement results have also indicated that when the reflector height is increased using stacked metals available in CMOS technology, the quality factor of the device is improved greatly. These designs, although not exhibiting the maximum possible quality factor of the device, was intended as a proof of concept that surface acoustic wave resonators can be implemented using CMOS with the minimum number of post-processes. Further development of this work indicates promising devices such as oscillators and filters for integration with circuits. The quality factor of the device can be further improved by increasing the number of reflectors and implementing methods to improve the piezoelectric coupling coefficient of the device.

The following references are incorporated herein in their entirety. Their numbering is reflected in the reference numerals used throughout the EXAMPLES section.

REFERENCES

[1] W. Buff, M. Rusko, E. Goroll, J. Ehrenpfordt, T. Vandahl, "Universal pressure and temperature SAW sensor for wireless applications," Ultrasonics Symposium, 1997. Proceedings., 1997 IEEE, vol. 1, no. pp. 359-362 vol. 1, 5-8 Oct. 1997

[2] P. Smole, W. Ruile, C. Korden, A. Ludwig, E. Quandt, S. Krassnitzer, P. Pongratz, "Magnetically tunable SAW-resonator," Frequency Control Symposium and PDA Exhibition Jointly with the 17th European Frequency and Time Forum, 2003. Proceedings of the 2003 IEEE International, vol., no. pp. 903-906, 4-8 May 2003

[3] A. Pohl, G. Ostermayer, F. Seifert, "Wireless sensing using oscillator circuits locked to remote high-Q SAW resonators," Ultrasonics, Ferroelectrics and Frequency Control, IEEE Transactions on, vol. 45, no. 5 pp. 1161-1168, September 1998

[4] T. Nomura, R. Takebayashi, A. Saitoh, "Chemical sensor based on surface acoustic wave resonator using Langmuir-Blodgett film", Ultrasonics, Ferroelectrics and Frequency Control, IEEE Transactions on, vol. 45, no. 5 pp. 1261-1265, September 1998.

[5] S. Datta, "Resonators", Prentice Hall, 1986, Ch. 10, pp. 225-239.

[6] Ruby, R. C.; Bradley, P.; Oshmyansky, Y.; Chien, A.; Larson, J. D., III, "Thin film bulk wave acoustic resonators (FBAR) for wireless applications," Ultrasonics Symposium, 2001 IEEE, vol. 1, no. pp. 813-821 vol. 1, 2001

[7] J. H. Visser, "Surface acoustic wave filter in ZnO—SiO2-Si layered structures: Design, technology and monolithic integration with electronic circuitry," Ph.D. dissertation, Delft University of Technology. Delft, the Netherlands, December 1989.

[8] M. J. Vellekoop, G. W. Lubking, A. Venema, "Acoustic-wave based monolithic microsensors", Invited, Proc. IEEE Ultrasonics Symposium, Cannes, France, (1994), pp. 565-574.

[9] A. G. Baca, E. J. Heller, V. M. Hietala, S. A. Casalnuovo, G. C. Frye-Mason, J. F. Klem, T. J. Dummond, "Development of a GaAs monolithic surface acoustic wave integrated circuit", IEEE J. Solid-State Circuits, vol. 34. no. 9, 1999

[10] A. N. Nordin, M. E. Zaghloul, "Design and Implementation of a 1 GHz Resonator Utilizing Surface Acoustic Wave," presented at the Int. Sym. Circuits and Systems, Kos, Greece, 2006.

[11] D. P. Morgan, "Analysis of Interdigital Transducers," Surface-Wave Devices for Signal Processing, New York: Elesevier Science, 1985, Ch. 4, pp. 57-105.

[12] P. T. M. van Zeijl, "Fundamental aspects and design of an FM upconversion receiver front-end with on-chip SAW filters," Ph.D. dissertation, Delft University of Technology. Delft, Netherlands, February 1990.

[13] S. Datta, B. J. Hunsinger, "An analytical theory for the scattering of surface acoustic waves by a single electrode in a periodic array on a piezoelectric substrate", J. Appl. Phys, vol. 51, pp. 4817-4823, 1980

[14] O. Tigli, M. E. Zaghloul, "Design and Fabrication of a Novel SAW Bio/Chemical Sensor in CMOS", in 2005 Proc. IEEE Sensors Conf., pp. 137-140.

[15] M. J. Vellekoop, "A Smart Lamb-Wave Sensor System", Ph.D. dissertation, Delft University of Technology. Delft, the Netherlands, December 1989.

[16] J Zhu, N W Emanetoglu, Y Chen, B V Yakshinskiy, Y Lu, "Wet-Chemical Etching of (112 0) ZnO Films", Journal of Electronic Materials; June 2004, vol. 33, no. 6, pp. 556-559.

[17] http://www.amis.com/pdf/C5_process_spec.pdf

[18] http://www.coventor.com

[19] http://www.cmicro.com/index.cfm/fuseaction/pg.view/pID/1172IEEE

[20] Standard definitions and methods of measurement for piezoelectric vibrators, ANSI/IEEE Standard 177, New York, N.Y., 1966.

[21] IEEE Standard on Piezoelectricity, ANSI/IEEE Standard 176, New York, N.Y., 1987.

It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. An integrated circuit device comprising:
a complementary metal oxide semiconductor (CMOS) device including a silicon substrate, and at least a first metal layer and a second metal layer overlaying the first metal layer;
an absorber formed from stacking the first metal layer, the second metal layer and polysilicon; and
a surface acoustic wave device comprising:
at least two interdigital transducers arranged in one of the first metal layer and the second metal layer; and
a piezoelectric material deposited over top of the at least two interdigital transducers, such that the interdigital transducers are embedded in the piezoelectric material.

2. The integrated circuit of claim 1, wherein the at least two interdigital transducers form a delay line.

3. The integrated circuit of claim 1, wherein the piezoelectric material is zinc oxide.

4. The integrated circuit of claim 1, further including an n-well in the silicon substrate, the n-well being operative as a heater.

5. An integrated circuit device comprising:
a complementary metal oxide semiconductor (CMOS) device including a silicon substrate having an n-well operative as a heater, and at least a first metal layer and a second metal layer overlaying the first metal layer; and
a surface acoustic wave device forming a delay line comprising:
at least two interdigital transducers arranged in the first metal layer;
an absorber formed from stacking the first metal layer, the second metal layer and polysilicon; and
a ZnO piezoelectric material deposited over top of the at least two interdigital transducers and the absorber, such that the interdigital transducers and the absorber are embedded in the piezoelectric material.

6. An integrated circuit device comprising:
a complementary metal oxide semiconductor (CMOS) device including a silicon substrate having at least a first metal layer and a second metal layer; and
a surface acoustic wave device forming a resonator comprising:
a shield formed in the first metal layer;
at least two interdigital transducers arranged in the second metal layer;
a reflector formed in a third metal layer; and
a ZnO piezoelectric material deposited over top of the shield, the at least two interdigital transducers and the reflector, such that the shield, the interdigital transducers and the reflector are embedded in the piezoelectric material.

7. The integrated circuit of claim 6, further including an n-well in the silicon substrate, the n-well being operative as a heater.

8. An integrated circuit device comprising:
a complementary metal oxide semiconductor (CMOS) device including a silicon substrate, and at least a first metal layer and a second metal layer overlaying the first metal layer; and
a first surface acoustic wave device forming a resonator comprising:
a shield in the first metal layer;
at least two interdigital transducers arranged in the second metal layer; and
a second acoustic wave device forming a delay line comprising:
at least two interdigital transducers arranged in the first metal layer; and
an absorber formed from stacking the first metal layer, the second metal layer and polysilicon;
wherein a piezoelectric material is deposited over top of the first and the second acoustic wave devices, such that the first acoustic wave device and the second acoustic wave device are embedded in the piezoelectric material.

9. The integrated circuit of claim 8, wherein the piezoelectric material is zinc oxide.

10. The integrated circuit of claim 8, further including an n-well in the silicon substrate, the n-well being operative as a heater.

11. An integrated circuit device comprising:
a complementary metal oxide semiconductor (CMOS) device including a silicon substrate, and at least a first metal layer and a second metal layer overlaying the first metal layer; and
a surface acoustic wave device comprising:
a metal shield layer formed in the first metal layer;
at least two interdigital transducers arranged in the second metal layer, the at least two interdigital transducers forming a resonator;
a reflector in a third metal layer; and
a piezoelectric material deposited over top of the at least two interdigital transducers, such that the interdigital transducers are embedded in the piezoelectric material.

12. The integrated circuit of claim 11, wherein the piezoelectric material is zinc oxide.

13. The integrated circuit of claim 11, further including an n-well in the silicon substrate, the n-well being operative as a heater.

* * * * *

UNITED STATES PATENT AND TRADEMARK OFFICE
CERTIFICATE OF CORRECTION

PATENT NO.      : 8,143,681 B2
APPLICATION NO. : 11/738460
DATED           : March 27, 2012
INVENTOR(S)     : Mona Zaghloul et al.

Page 1 of 1

It is certified that error appears in the above-identified patent and that said Letters Patent is hereby corrected as shown below:

At column 1, line 12, change

"This was supported in part by NFS under Grant 0225431."

to read as follows:

--This invention was made with government support under Grant 0225431 awarded by the National Science Foundation. The government has certain rights in the invention.--

Signed and Sealed this
Fifth Day of March, 2013

Teresa Stanek Rea
*Acting Director of the United States Patent and Trademark Office*